US009567332B2

(12) United States Patent
Bhirud et al.

(10) Patent No.: US 9,567,332 B2
(45) Date of Patent: Feb. 14, 2017

(54) PROCESS FOR THE PREPARATION AND PURIFICATION OF APIXABAN

(71) Applicants: GLENMARK PHARMACEUTICALS LIMITED, Mumbai (IN); GLENMARK GENERICS LIMITED, Mumbai (IN)

(72) Inventors: Shekhar Bhaskar Bhirud, Mumbai (IN); Sushanta Mishra, Bolangir (IN); Suresh Babu Narayanan, Thane (IN); Sachin Bhagwan Naykodi, Navi Mumbai (IN); Samir Naik, Thane (IN); Sachin Srivastava, Navi Mumbai (IN); Pramod Vitthal Patil, Panvel (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/761,084

(22) PCT Filed: Jan. 15, 2014

(86) PCT No.: PCT/IN2014/000029
§ 371 (c)(1),
(2) Date: Jul. 15, 2015

(87) PCT Pub. No.: WO2014/111954
PCT Pub. Date: Jul. 24, 2014

(65) Prior Publication Data
US 2015/0353543 A1    Dec. 10, 2015

Related U.S. Application Data

(60) Provisional application No. 61/772,541, filed on Mar. 5, 2013.

(30) Foreign Application Priority Data

Jan. 17, 2013   (IN) .......................... 156/MUM/2013

(51) Int. Cl.
*C07C 251/76*   (2006.01)
*C07D 471/04*   (2006.01)

(52) U.S. Cl.
CPC .......... *C07D 471/04* (2013.01); *C07C 251/76* (2013.01)

(58) Field of Classification Search
CPC .......................... C07D 471/04; C07C 251/76
(Continued)

(56) References Cited

U.S. PATENT DOCUMENTS 6,919,451 B2    7/2005  Zhou et al.
6,967,208 B2   11/2005  Pinto et al.
2010/0130543 A1*  5/2010  Gant .................... C07D 471/04
                                                     514/303

FOREIGN PATENT DOCUMENTS

CN    101967145    7/2012
CN    102675314    9/2012
(Continued)

OTHER PUBLICATIONS

Jiang; Synthetic Communications 2013, 43, 72-79.*
(Continued)

*Primary Examiner* — Noble Jarrell
*Assistant Examiner* — Daniel Carcanague
(74) *Attorney, Agent, or Firm* — Ryan, Mason & Lewis, LLP

(57) ABSTRACT

The present invention provides a process for the preparation and purification of apixaban.

14 Claims, 3 Drawing Sheets

Figure 1:
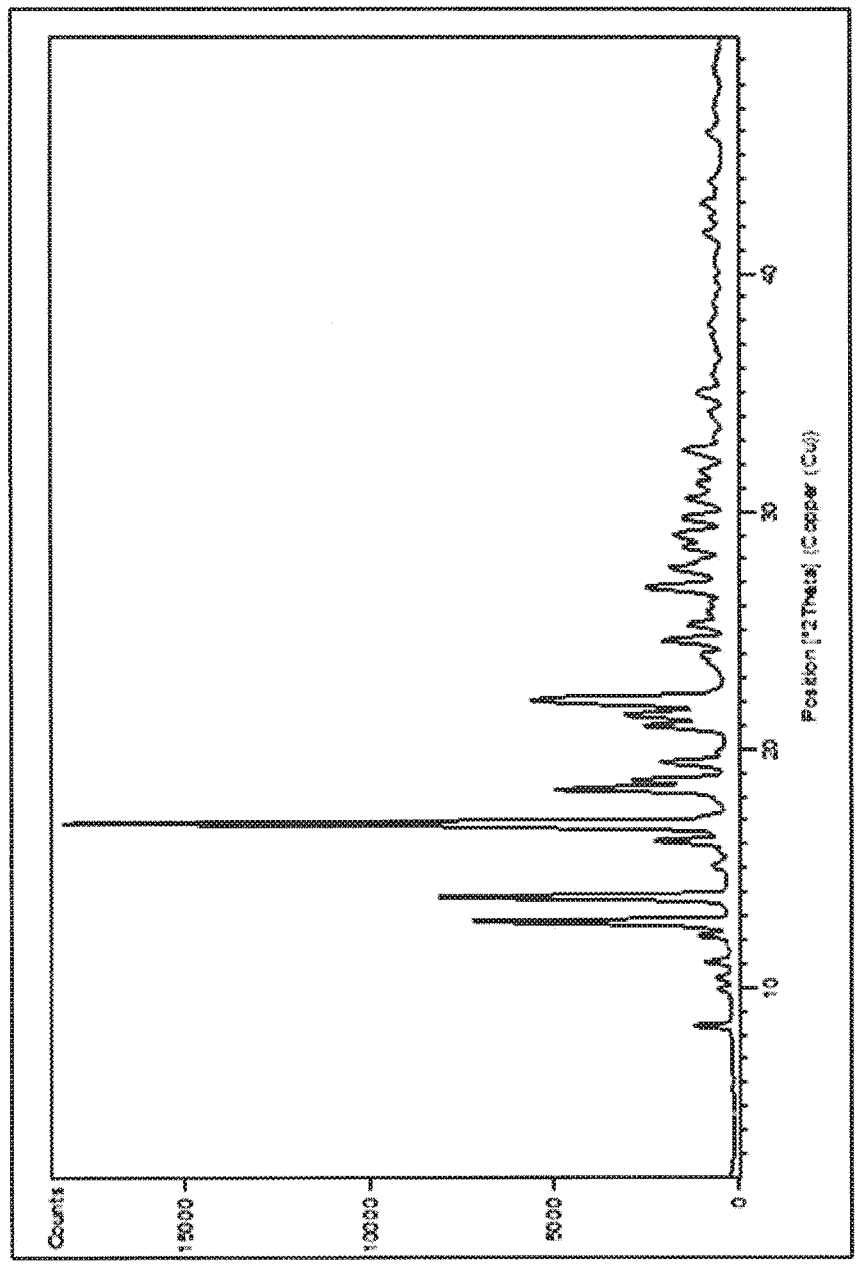

(58) Field of Classification Search
USPC .......................................................... 546/120
See application file for complete search history.

(56) References Cited

FOREIGN PATENT DOCUMENTS

| | | |
|---|---|---|
| WO | 03049681 A2 | 6/2003 |
| WO | 2006078331 A2 | 7/2006 |

OTHER PUBLICATIONS

Wuts and Greene; "Greene's Protective Groups in Organic Synthesis", 4th Ed, 2007, Wiley & Sons, chapter 3, pp. 367-430.*

* cited by examiner

PROCESS FOR THE PREPARATION AND PURIFICATION OF APIXABAN

PRIORITY

This application claims priority under 35 U.S.C. §371 to International Application No. PCT/IN2014/000029, filed Jan. 15, 2014 which claims the benefit under 35 U.S.C. §119 to Indian Provisional Application No. 156/MUM/2013, filed on Jan. 17, 2013, and U.S. Provisional Application No. 61/772,541 filed on Mar. 5, 2013, the contents of which are incorporated herein by reference.

FIELD OF THE INVENTION

The present invention relates to a process for preparation and purification of apixaban.

BACKGROUND OF THE INVENTION

Apixaban, chemically known as 1-(4-methoxyphenyl)-7-oxo-6-[4-(2-oxopiperidin-1-yl) phenyl]-4,5,6,7-tetrahydro-1H-pyrazolo[3,4-c]pyridine-3-carboxamide is represented by the structural formula,

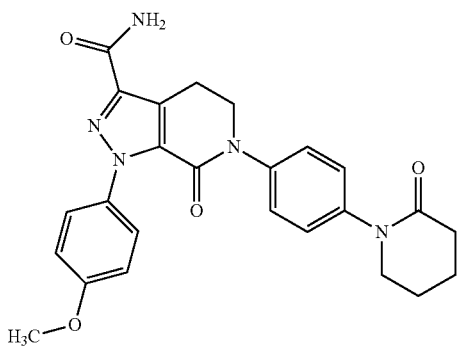

I

Apixaban belongs to a group of medicines called anticoagulants. Apixaban is commercially available as Eliquis® in the form of pharmaceutical preparations. Eliquis® is a factor Xa inhibitor anticoagulant indicated to reduce the risk of stroke and systemic embolism in patients with nonvalvular atrial fibrillation.

U.S. Pat. No. 6,967,208 discloses apixaban and the process for its preparation which utilizes flash chromatography for product isolation.

U.S. Pat. No. 6,919,451 discloses process for preparation of 1-(4-methoxy-phenyl)-7-oxo-6-[4-(2-oxo-piperidin-1-yl)-phenyl]-4,5, 6,7-tetrahydro-1H-pyrazolo [3,4-c]pyridine-3-carboxylic acid ethyl ester by flash column chromatography.

These prior art processes are not suitable for large scale productions because they require laborious chromatographic purification with subsequent low product yields.

Presently, we have developed a cost effective, industrially feasible process for the preparation and purification of apixaban which is less time consuming.

SUMMARY OF THE INVENTION

In one embodiment, the present invention provides a process for the preparation of a compound of formula I,

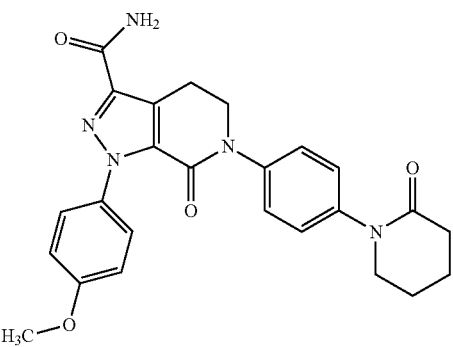

I comprising:

a) deprotecting a compound of formula IX, wherein R is selected from the group consisting of phenyl, optionally substituted phenyl, benzyl, optionally substituted benzyl, allyl, trityl, silyl or C(O)R1, wherein R1 is H, loweralkyl; and

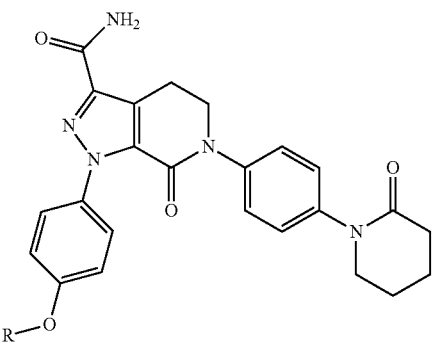

IX

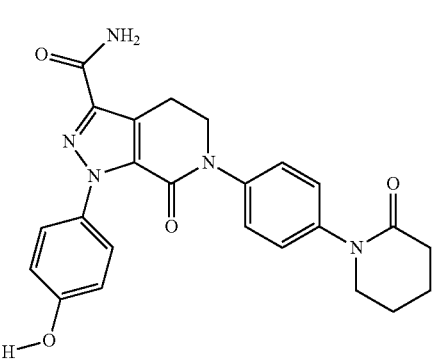

X b) methylating the compound of formula X to obtain apixaban, a compound of formula I.

In one embodiment, the present invention provides a process for the preparation of apixaban, a compound of formula I, comprising:

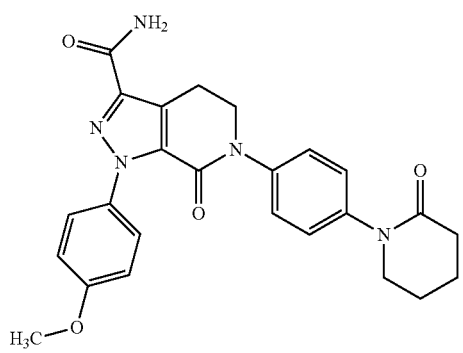

I isolating apixaban from a mixture of water and an organic solvent selected from the group consisting of alcohols, ethers, amides, esters, nitriles, sulfoxides, ketones, hydrocarbons, acetates and halogenated hydrocarbons.

In one embodiment, the present invention provides a process for the purification of apixaban, a compound of formula I, comprising treating crude apixaban with a base.

In one embodiment, the present invention provides use Of a compound selected from the following:

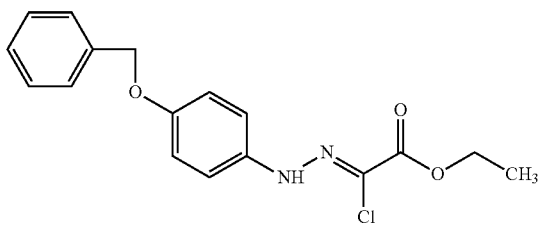

VIII in the preparation of apixaban.

In one embodiment, the present invention provides a compound selected from the following:

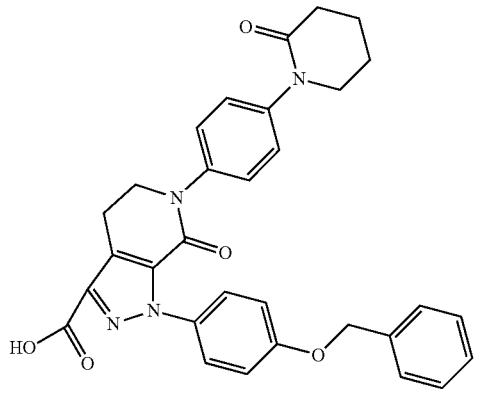

VI

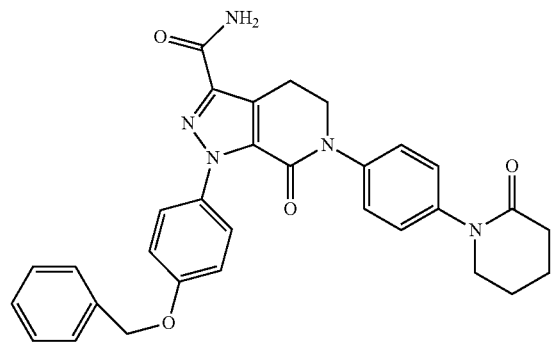

VI

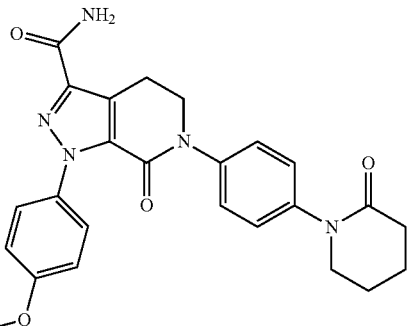

IXa

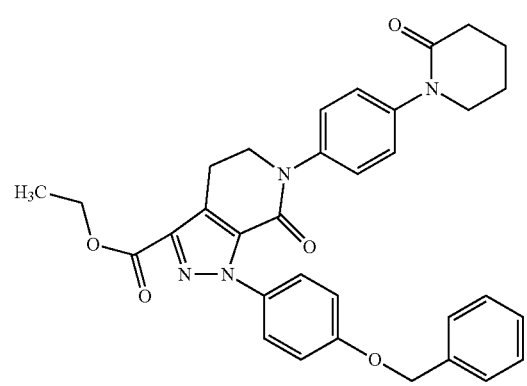

IXa

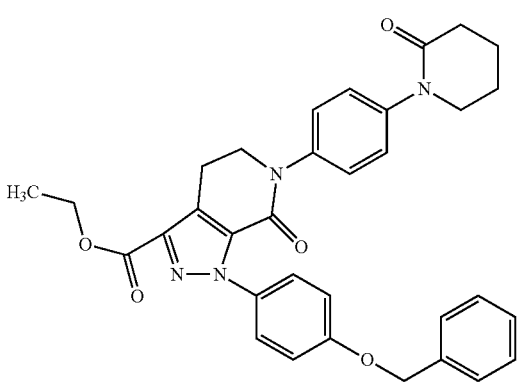

VII

VII

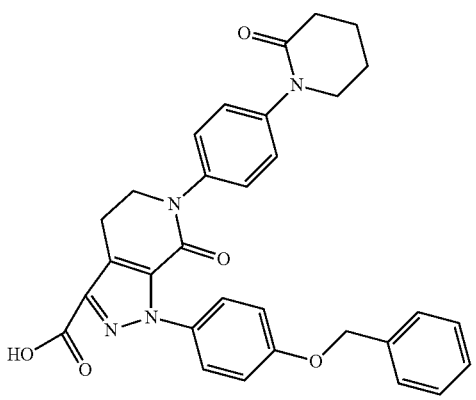

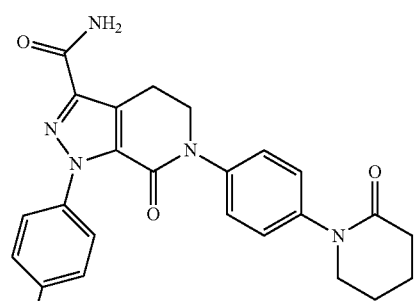

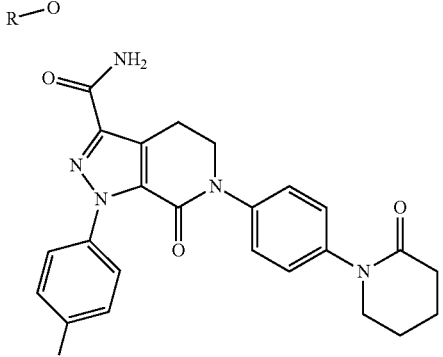

BRIEF DESCRIPTION OF THE ACCOMPANYING FIGURES

FIG. 1: PXRD pattern of apixaban, which is substantially in accordance with example III.

Figure 2:
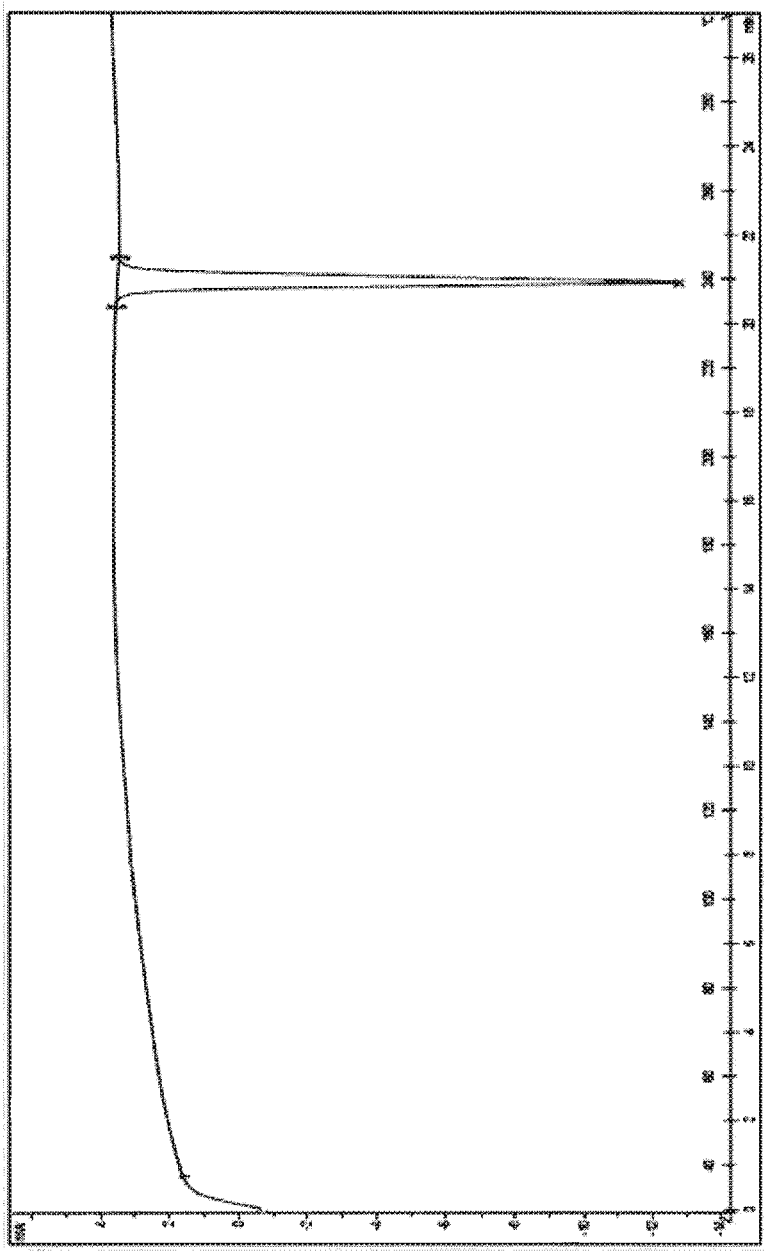

FIG. 2: DSC pattern of apixaban, which is substantially in accordance with example III.

Figure 3:
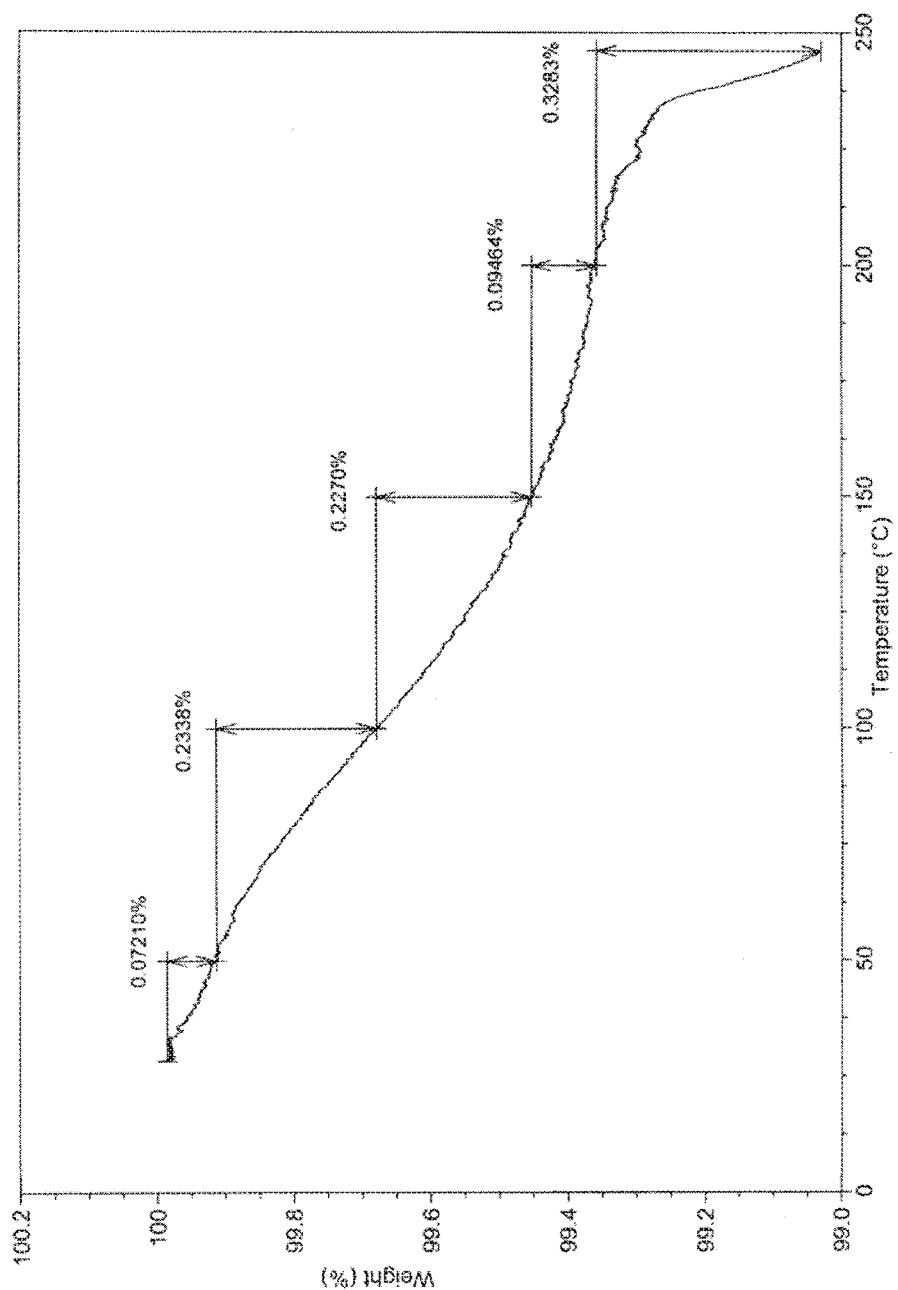

FIG. 3: TGA of apixaban, which is substantially in accordance with example III.

DETAILED DESCRIPTION OF THE INVENTION

In one embodiment, the present invention provides a process for the preparation of a compound of formula I,

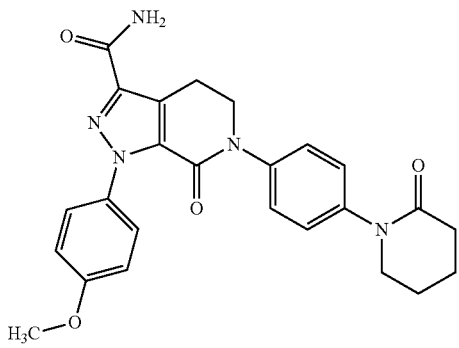

comprising:
a) deprotecting a compound of formula IX, wherein R is selected from the group consisting of phenyl, optionally substituted phenyl, benzyl, optionally substituted benzyl, allyl, trityl, silyl or C(O)R1, wherein R1 is H, loweralkyl, to obtain a compound of formula X; and methylating the compound of formula X to obtain apixaban, a compound of formula I.

The term "loweralkyl" refers to methyl, ethyl, isopropyl, n-propyl, isopropyl, n-butyl, isobutyl, tert-butyl, n-pentyl and the like;

The term "optionally substituted phenyl" includes substituents selected from the group consisting of nitro, halo such as chloro, bromo, iodo, alkoxy such as p-methoxy, alkyl includes methyl, ethyl, propyl, butyl and the like;

The term "optionally substituted benzyl" includes substituents selected from the group consisting halo, alkyl, alkoxy or nitro group wherein halo includes Cl, Br, I; alkyl includes methyl, ethyl, propyl, butyl; alkoxy includes methoxy, ethoxy, propoxy and the like.

The term "silyl" refers to triloweralkylsilyl such as trimethylsilyl, triethylsilyl and the like.

In one embodiment, in step a) of the above process deprotection may be carried out by any of the following:
a) when R1 is H, loweralkyl, the deprotection is performed using an inorganic acid selected from the group consisting of hydrochloric acid, hydrobromic acid, sulfuric acid, phosphoric acid; inorganic base selected from the group consisting of hydroxides such as sodium hydroxide, potassium hydroxide, carbonates such as sodium carbonate, potassium carbonate.
b) when R is phenyl, optionally substituted phenyl, benzyl, optionally substituted benzyl, trityl or allyl the deprotection of the compound of formula I is performed by hydrogenation.
c) when R is silyl, the deprotection of the compound of formula I is performed using acids such as acetic acid or fluorides such as tetrabutylammonium fluoride.

In one embodiment, the deprotection reaction may be carried out in presence of a suitable solvent selected from the group consisting of alcohols such as methanol, isopropanol, ethanol and the like; hydrocarbons such as toluene, xylene and the like; halogenated solvents such as methylene dichloride, ethylene dichloride and the like; esters such as ethyl acetate, propyl acetate, isopropyl acetate; ethers such as tetrahydrofuran, diisopropyl ether, diethyl ether and the like. Preferably the solvent is methanol.

In one embodiment, in step a) of the above process R is benzyl, a compound of formula IXa.

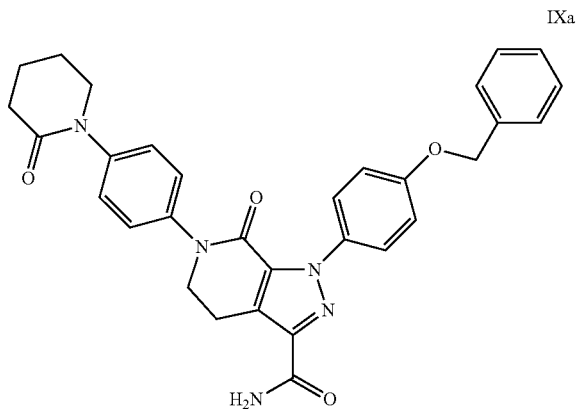 [SMILES: NC(=O)c1nn(-c2ccc(OCc3ccccc3)cc2)c2c1CCN(c1ccc(N3CCCCC3=O)cc1)C2=O]

In one embodiment, in step a) R is benzyl, the deprotection is carried out by hydrogenation.

In one embodiment, hydrogenation is carried out in presence of a suitable catalyst. The catalyst may be selected from the group consisting of palladium, platinum, nickel, rhodium or alumina.

The palladium catalyst, may be in the form of palladium on carbon or palladium salts such as palladium hydroxide, palladium hydroxide on carbon, and the like; most preferably, the hydrogenation catalyst is palladium on carbon. The palladium content in the catalyst may be about 5% to about 20% wt/wt % on carbon, preferably about 10% wt/wt % on carbon.

The pressure for hydrogenation can range from about 1 kg/cm$^2$g to about 30 kg/cm$^2$g by using hydrogen gas, preferably about 5kg/cm$^2$g to about 20kg/cm$^2$g, more preferably about 5kg/cm$^2$g to about 10 kg/cm$^2$g.

The reaction may be carried out at a temperature of about 25° C. to about reflux temperature of the solvent. The reaction is carried out over a period of about 10 to about 30 hours. Preferably, the deprotection reaction is carried out in methanol at a temperature of about 45° C. to about 50° C. over a period of about 18 to about 22 hours to obtain a compound of formula X. The catalyst in the reaction mixture may be separated or recovered from the reaction mixture by methods known in the art. The filtrate containing the product may be concentrated and the residue may be extracted with an organic solvent under basic condition by adjusting the pH, wherein the organic solvent may be selected from halogenated solvents such as dichloromethane, dichloroethane, chloroform, carbon tetrachloride and the like, hydrocarbons such as n-hexane, n-heptane, cyclohexane, benzene, toluene and the like; esters such as methyl acetate, ethyl acetate, isopropyl acetate, tertiary butyl acetate and the like; ethers such as diethyl ether, diisopropyl ether, methyl tertiary butyl ether and the like; and mixtures thereof. Preferably the organic solvent is dichloromethane.

The pH may be adjusted with bases such as sodium hydroxide, potassium hydroxide, triethylamine, pyridine and the like. Preferably the base is triethylamine. The compound of formula X is isolated after work up by standard techniques such as extraction, evaporation, filtration, distillation and the like.

In one embodiment, in step b) of the above process the compound of formula X is methylated using a suitable methylating agent selected from the group consisting of dimethyl sulphate, methyl iodide and dimethylcarbonate.

In one embodiment, in step b) of the above process the compound of formula X is methylated using a suitable methylating agent in presence of a suitable base and a suitable solvent.

Suitable base may be organic or inorganic bases. Inorganic base may be selected from the group consisting of hydroxides such as sodium hydroxide, potassium hydroxide, calcium hydroxide, lithium hydroxide; alkoxides such as sodium methoxide, potassium methoxide, sodium tert-butoxide, potassium tert-butoxide; carbonates such as sodium carbonate, potassium carbonate, bicarbonates such as sodium bicarbonate, potassium bicarbonate and the like. Organic bases may be selected from the group consisting of triethyl amine, trimethyl amine, pyridine, diisopropyl ethyl amine, pyridine and dimethyl amino pyridine. Preferably, reaction is carried out in the presence of potassium carbonate.

Suitable solvents include but are not limited to water, ethers such as tetrahydrofuran, diethyl ether and diisopropyl ether; esters such as ethyl acetate, isopropyl acetate, butyl acetate; halogentaed solvents such as ethylene dichloride, methylene dichloride, chloroform, carbon tetrachloride; alcohols such as methanol, ethanol, n-propanol, 2-propanol; hydrocarbons such as toluene, benzene, cyclohexane; ketones such as acetone, methyl ethyl ketone, methyl tert-butyl ketone or mixtures thereof. Preferably the reaction is carried out in acetone.

In one embodiment, compound of formula X is methylated using dimethyl sulphate in acetone in the presence of potassium carbonate.

The reaction may be carried out at a temperature of about 20° C. to about 40° C. The reaction transpires over a period of about 2-6 hours. Preferably, the reaction is carried out at a temperature of about 25-30° C. over a period of about 3 to 5 hour.

In one embodiment, the present invention provides a process for the preparation of compound of formula I, comprising:

a) deprotecting a compound of formula IXa by hydrogenation process to obtain a compound of formula X; and b) methylating the compound of formula X to obtain a compound of formula I.

In one embodiment, in step a) of the above process compound of formula IXa is subjected to hydrogenation using Pd/C under hydrogen pressure. The reaction is carried out in presence of methanol at a temperature of about 45 to about 50° C.

In one embodiment, in step b) of the above process compound of formula X is methylated using dimethyl sulphate in acetone in presence of potassium carbonate.

In one embodiment, the compound of formula IXa is prepared by a process comprising;

a) reacting a compound of formula II with a compound of formula VI to obtain a compound of formula VII, and

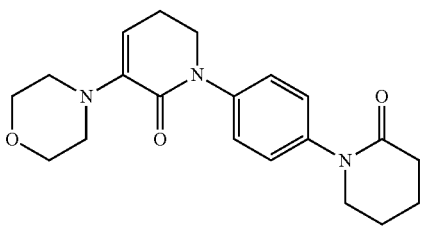

II

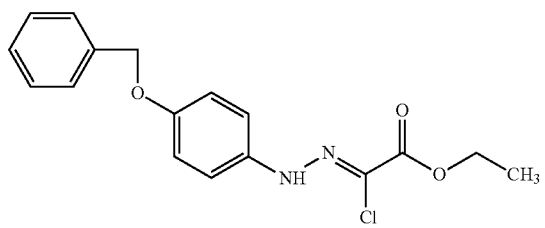

VI b) converting the compound of formula VII to a compound of formula IXa.

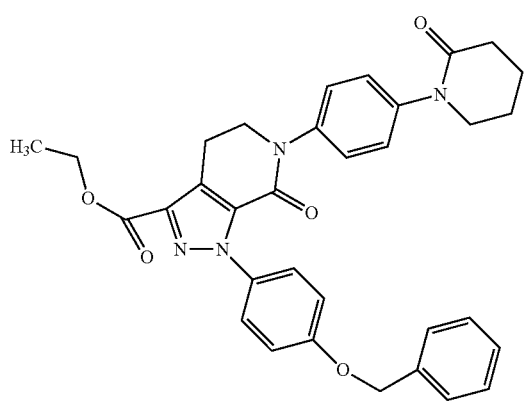

VII

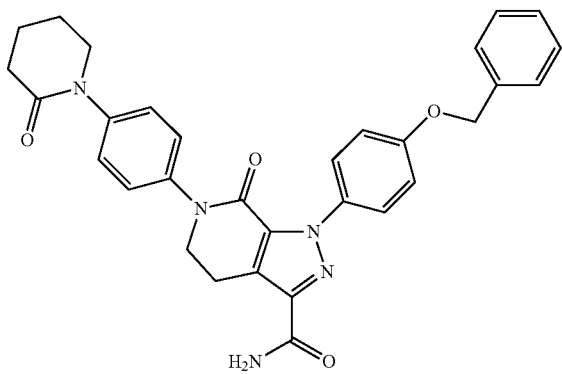

IXa

In one embodiment, in step a) of the above process compound of formula II is reacted with a compound of formula VI.

The reaction may be carried out in the presence of a suitable base and a suitable solvent.

Suitable base may be organic or inorganic bases. Inorganic base may be selected from the group consisting of hydroxides such as sodium hydroxide, potassium hydroxide, calcium hydroxide, lithium hydroxide; alkoxides such as sodium methoxide, potassium methoxide, sodium tert-butoxide, potassium tert-butoxide; carbonates such as sodium carbonate, potassium carbonate, bicarbonates such as sodium bicarbonate, potassium bicarbonate and the like. Organic bases may be selected from the group consisting of triethyl amine, trimethyl amine, pyridine, diisopropyl ethyl amine, pyridine and dimethyl amino pyridine. Preferably, reaction is carried out in the presence of triethylamine.

Suitable solvents include but are not limited to water, ethers such as tetrahydrofuran, diethyl ether and diisopropyl ether; esters such as ethyl acetate, isopropyl acetate, butyl acetate; halogenated solvents such as ethylene dichloride, methylene dichloride, chloroform, carbon tetrachloride; alcohols such as methanol, ethanol, n-propanol, 2-propanol; hydrocarbons such as toluene, benzene, cyclohexane; ketones such as acetone, methyl ethyl ketone, methyl tert-butyl ketone or mixtures thereof Preferably the reaction is carried out in ethylacetate.

In one embodiment, the compound of formula II is reacted with a compound of formula VI in ethylacetate in the presence of triethylamine.

In one embodiment, the reaction may be optionally carried out in presence of a suitable catalyst such as potassium iodide.

The reaction may be carried out at a temperature of about 30° C. to about reflux temperature of the solvent. The reaction transpires over a period of about 5 to about 20 hours. Preferably, the reaction transpires at reflux temperature of the solvent over a period of about 10-15 hours.

The reaction mixture is cooled to a temperature of about −5 to about 20° C. and treated with a suitable acid which include, but are not limited to, mineral acids selected from hydrochloric acid, orthophosphoric acid, trifluoroacetic acid, trifluoromethane sulfonic acid, methane sulfonic acid, nitric acid, sulfuric acid or the mixtures thereof or their aqueous mixtures. Preferably the acid used is aqueous hydrochloric acid.

The compound of formula VII is isolated from the reaction mixture using standard techniques such as extraction, distillation, concentration, filtration and the like.

In one embodiment, in step b) of the above process compound of formula VII is converted to a compound of formula IXa.

In one embodiment, the compound of formula VII is converted to a compound of formula IXa, in the presence of a suitable base and suitable solvent using suitable ammonia-generating agents.

Suitable ammonia generating agents may be selected from the group consisting of ammonium formate, formamide, aqueous ammonia and the like. Preferably, the ammonia generating agent is formamide. Suitable solvent may be selected from the group consisting of amide such as dimethyl formamide, dimethyl acetamide; hydrocarbons such as toluene, xylene; halogentaed solvents such as methylene dichloride, ethylene dichloride and the like; sulphoxide such as dimethyl sulphoxide (DMSO). Preferably, the solvent is dimethylformamide.

Suitable base may be selected from the group consisting of hydroxides such as sodium hydroxide, potassium hydroxide; carbonates such as potassium carbonate, sodium carbonate, alkoxides such as sodium methoxide, potassium methoxide, sodium tertiary butoxide and the like. Preferably, the base used is sodium methoxide.

In one embodiment, the compound of formula VII is converted to the compound of formula IXa in the presence formamide and sodium methoxide in N, N-dimethyl formamide.

The reaction is carried out at a temperature of about 20° C. to about reflux temperature of the solvent. The reaction transpires over a period of about 30 min to about 5 hours. Preferably, the reaction is carried out a temperature of about 25-30° C. over a period of about 1 to 3 hours.

In one embodiment, in step b) of the above process compound of formula VII is hydrolysed to obtain a compound of formula VIII and then amidated to obtain a compound of formula IXa.

In one embodiment, compound of formula VII is hydrolysed using suitable acid such as hydrochloric acid, sulphuric acid and the like or suitable base such as hydroxide for example sodium hydroxide, potassium hydroxide; alkoxides such as sodium methoxide, potassium methoxide, potassium tert butoxide and the like. Preferably, compound of formula VII is hydrolysed using sodium hydroxide to obtain a compound of formula VIII.

VIII

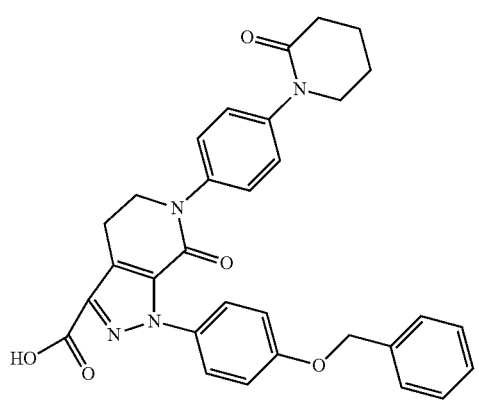

In one embodiment, the compound of formula VII is hydrolysed using sodium hydroxide in the presence of a suitable solvent.

Suitable solvent may be selected from the group consisting of alcohols such as methanol, ethanol, isopropanol and the like; ketones such as acetone, methyl ethyl ketone, methyl isobutyl ketone and the like;, halogenated solvents such as methylene chloride, ethylene chloride and the like; hydrocarbons such as toluene, xylene; dioxane, ethers such as tetrahydrofuran, diethyl ether, diisopropyl ether, methyl tertiary butyl ether and water or mixtures thereof Preferably, the solvent is methanol.

In one embodiment, in step a) of the above process compound of formula VII is hydrolysed in presence of sodium hydroxide in methanol to obtain a compound of formula VIII.

The hydrolysis reaction may be carried out at a temperature of about 20-40° C. The reaction transpires over a period of about 1-7 hours. Preferably, the reaction is carried out at a temperature of about 25-30° C. over a period of about 2-4 hours.

The compound of formula VIII may be isolated by methods known in the art such as filtration, centrifugation and the like.

The compound of formula VIII is amidated using ammonia in the presence of an alkyl or aryl haloformate or a suitable acid chloride, a suitable base and a suitable solvent to obtain a compound of formula IXa.

The alkyl or aryl haloformate may be selected, from but are not limited to methyl chloroformate, ethyl chloroformate, isobutyl chloroformate and benzyl chloroformate. Preferably, the alkyl chloroformate is isobutyl chloroformate.

The suitable acid chlorides may be selected from, but are not limited to thionyl chloride, oxalyl chloride,pivolyl chloride.

Suitable solvent may be selected from the group consisting of esters such as ethyl acetate, butyl acetate, isopropyl acetate; ethers such as tetrahydrofuran, diethyl ether, diisopropyl ether; chlorinated solvents such as methylene dichloride, ethylene dichloride; hydrocarbons such as toluene, xylene; polar aprotic solvents such as dimethyl formamide, dimethyl acetamide, dimethyl sulfoxide, N-methyl pyrrolidine or mixtures thereof Preferably the reaction is carried out in ethyl acetate.

Suitable base may be selected from organic bases or inorganic bases. Organic bases may be selected from, but are not limited to N-methyl morpholine, di-isopropyl ethylamine, triethylamine, dimethyl amino pyridine, trimethylamine, pyridine, picoline and the like. Inorganic bases may be selected from sodium hydroxide, potassium hydroxide, calcium hydroxide, lithium hydroxide; alkoxides such as sodium methoxide, potassium methoxide, sodium tert-butoxide, potassium tert-butoxide; carbonates such as sodium carbonate, potassium carbonate, bicarbonates such as sodium bicarbonate, potassium bicarbonate and the like. Preferably, the reaction is carried out in presence of triethyl amine.

In one embodiment, the compound of formula VIII is reacted with ammonia in the presence of isobutyl chloroformate and triethylamine in ethyl acetate to obtain a compound of formula IXa.

In one embodiment, the compound of formula IXa may be converted to a compound of formula I by a process as described herein above.

In one embodiment, the present invention provides a process for the purification of apixaban, compound of formula I,

I

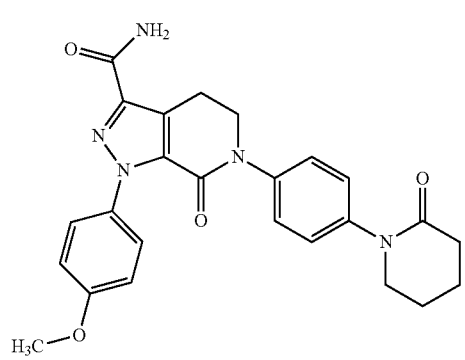

comprising treating crude apixaban with a base.

A suitable base may be selected from an organic or an inorganic base. The inorganic base may be selected from the group consisting of hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like. The organic base may be selected from triethyl amine, trimethyl amine, diisopropyl ethylamine, dimethyl amino pyridine, picoline, dimethyl amino pyridine and pyridine. Preferably, the base is sodium hydroxide.

The purification may be carried out in presence of a suitable solvent or mixtures thereof.

A suitable solvent may be selected from the group consisting of alcohols such as methanol, ethanol, isopropanol and the like; ethers such as diethyl ether, diisopropyl ether, methyl tertiary butyl ether and the like; amides such as dimethyl acetatmide, dimethyl formamide and the like, esters such as ethyl acetate, isopropyl acetate, propyl acetate and the like; nitriles such as acetonitrile, butyronitrile and the like; sulfoxides such as dimethyl sulfoxide; ketones suchas acetone, methyl ethyl ketone, methyl isobutyl ketone and the like; hydrocarbons such as toluene, xylene and the like; halogenated hydrocarbons such as methylene dichloride, ethylene dichloride, carbon tetrachloride and the like; water and mixtures thereof. Preferably, the solvent is a mixture of methylene dichloride and methanol.

In one embodiment the present invention provides a process for purification of apixaban comprising dissolving apixaban in a solvent mixture of methylene dichloride and methanol. The solution is treated with aqueous alkali hydroxide. Preferably, the solution containing apixaban is treated with aqueous sodium hydroxide solution. Apixaban is isolated by methods known in the art such as concentration, distillation and the like. Preferably, apixaban is isolated by concentration.

In one embodiment, the term "crude" refers to apixaban having a purity of atleast 90% as measured by HPLC (High performance liquid chromatography).

In one embodiment, the impurity of formula V and VIII is eliminated by treating the crude apixaban with a base.

In one embodiment, the present invention provides a' process for preparing apixaban having a purity of atleast 95%, wherein the process comprising treating crude apixaban with a base.

In one embodiment, the present invention provides a process for preparing apixaban having a purity of atleast 98%, wherein the process comprising treating crude apixaban with a base.

In one embodiment, the present invention provides a process for preparing apixaban having a purity of atleast 99%, wherein the process comprising treating crude apixaban with a base.

The present invention provides a process for the preparation of apixaban, a compound of formula I, comprising:

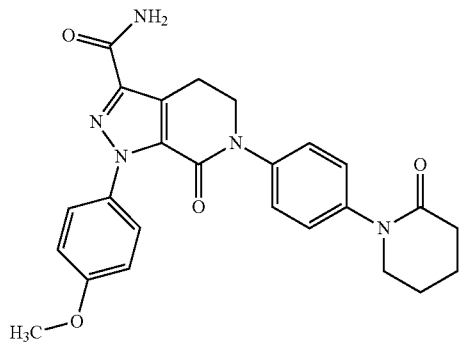

I isolating apixaban from a mixture of water and an organic solvent selected from the group consisting of alcohols, ethers, amides, esters, nitriles, sulfoxides, ketones, hydrocarbons, acetates and halogenated hydrocarbons.

The alcohol may be selected from C1-C5 alcoholic solvent group consisting of methyl alcohol, ethyl alcohol, propyl alcohol, isopropyl alcohol, butyl alcohol, tertiary butyl alcohol and the like. Preferably the alcohol may be isopropyl alcohol or its mixture with other alcohols; ethers may be selected from the group consisting of tetrahydrofuran, isopropyl ether, methyl tertiary-butyl ether, diethyl ether and the like; amides may be selected from dimethyl formamide, dimethyl acetamide; esters may be selected from the group consisting of isopropyl acetate, ethyl acetate, butyl acetate and the like; nitriles may be selected from the group consisting of acetonitrile, propionitrile, butyronitrile and the like; sulfoxides such as dimethyl sulfoxide; ketones may be selected from the group consisting of acetone, methyl ethyl ketone, methyl isobutyl ketone and the like; hydrocarbons may be selected from the group consisting of n-hexane, n-heptane, toluene, xylene and the like; acetates may be selected from the group consisting of methyl acetate, ethyl acetate, isopropyl acetate, butyl acetate and the like; halogenated solvents may be selected from the group consisting of methylene dichloride, ethylene dichloride, chloroform, carbon tetrachloride and the like.

In one embodiment, the present invention provides a process for the preparation of apixaban comprising:
a) treating apixaban with a mixture of water and an organic solvent selected from the group consisting of alcohols, ethers, amides, esters, nitriles, sulfoxides, ketones, hydrocarbons, acetates and halogenated hydrocarbons to form a mixture;
b) optionally heating the mixture of step 'a'; and
c) crystallizing apixaban from the mixture.

In one embodiment, in step a) of the above process, apixaban is dissolved or suspended in a mixture of water and an organic solvent. Preferably, the organic solvent is a ketone.

In one embodiment, in step b) of the process, the reaction mixture containing apixaban, ketone and water is heated to reflux temperature to obtain a clear solution. The reaction mixture is maintained at about reflux temperature for a period of about, 30 minutes to about 180 minutes. Preferably, the reaction mixture is maintained at about reflux temperature for a period of about 60 minutes.

In one embodiment, in step c) of the above process apixaban is crystallized from the reaction mixture by cooling the reaction mixture to a temperature of about −5 to −20° C. Preferably, the reaction mixture is cooled to about 10-15° C. Apixaban is isolated from the reaction mixture by methods known the in the art which include filtration, centrifugation and evaporation. Preferably, apixaban is isolated by filtration.

As used herein the term "treating" refers to contacting, suspending or slurrying.

In one embodiment, the present invention provides a process for the preparation of apixaban comprising suspending apixaban in a mixture of acetone and water. The reaction mixture is heated to reflux temperature to obtain a solution. The solution is maintained at about reflux temperature for a period of about 60 minutes. The solution is gradually cooled to about 10-15° C. and the precipitated apixaban is isolated by filtration.

In one embodiment, the present invention provides a process for the preparation of apixaban comprising:
a) dissolving apixaban in a solvent selected from the group consisting of alcohols, ethers, amides, esters, nitriles, sulfoxides, ketones, hydrocarbons, acetates and halogenated hydrocarbons to form a solution;
b) adding water as an anti-solvent to the solution; and
c) crystallising apixaban from the above step 'b'.

In one embodiment, the present invention provides a process for the preparation of apixaban comprising isolating apixaban from a mixture of DMSO and water.

In one embodiment, the present invention provides a process for the preparation of apixaban wherein apixaban is dissolved in DMSO and water is added as an anti-solvent.

In one embodiment, in step a) of the above process, the reaction mixture containing apixaban in a sulfoxide such as dimethyl sulfoxide is dissolved by heating to a temperature of about 35° C. to about reflux temperature. Preferably, the reaction mixture is heated to about 75-80° C. to obtain a clear solution. The solution is maintained for a period of about 15 minutes to about 90 minutes. Preferably, the reaction mixture is maintained for a period of about 30 minutes.

In one embodiment, in step b) of the above process water is added as an anti-solvent to the solution of step 'a'.

In one embodiment, in step c) of the above process apixaban is crystallized from the reaction mixture by cooling the reaction mixture to a temperature of about −20° C. to about 40° C.

Preferably, the reaction mixture is cooled to a temperature of about 25-30° C. Apixaban is isolated from the reaction mixture by methods known the in the art which include filtration, centrifugation and evaporation. Preferably, apixaban is isolated by filtration.

In one embodiment, the present invention provides a process for the preparation of apixaban wherein apixaban is dissolved in dimethyl formamide and water is added as an anti-solvent.

In one embodiment, the present invention provides purification of apixaban by acid base treatment, which allows it to be purified by conversion into inorganic or organic acid salts by reacting with the respective acids to form salts and back to the apixaban.

Suitable acids may be selected from the group consisting of hydrochloric acid, sulphuric acid, phosphoric acid, hydrobromic acid, succinic acid, oxalic acid, formic acid, acetic acid and the like.

In one embodiment, the present invention provides a process of preparation of apixaban by solvent/anti-solvent method.

A suitable solvent may be selected from a non-carboxylic solvent such as water, alcohols, ethers, esters, amides, nitriles, sulfoxides, ketones, hydrocarbons, acetates and halogenated hydrocarbons and a suitable anti-solvent may be selected from water, aliphatic hydrocarbons and the like.

In one embodiment, the present invention provides a process for the preparation of apixaban comprising isolating apixaban from a mixture of DMSO and water, wherein the compound of formula VII or VIII is less than 0.1% w/w of apixaban, as measured by HPLC (high performance liquid chromatography).

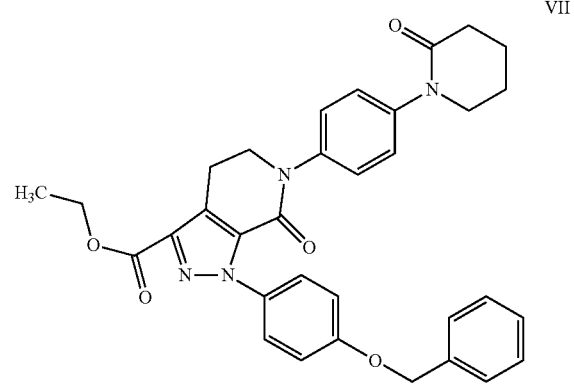

VII

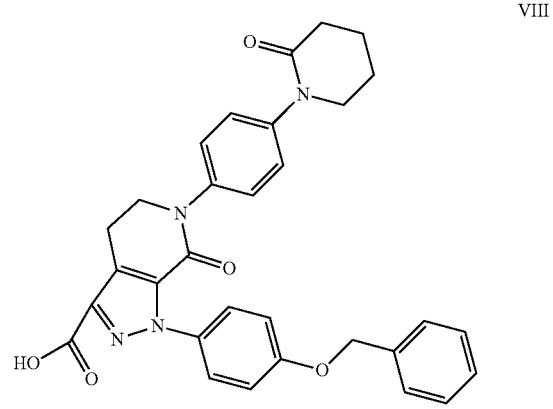

VIII

In one embodiment the present invention provides use of a compound selected from the following:

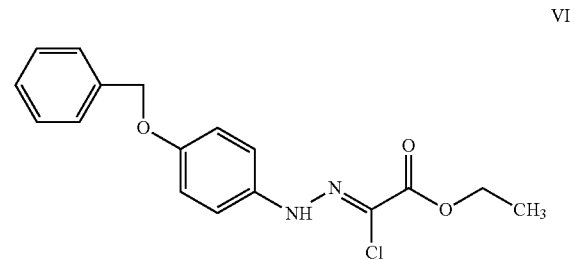

VI

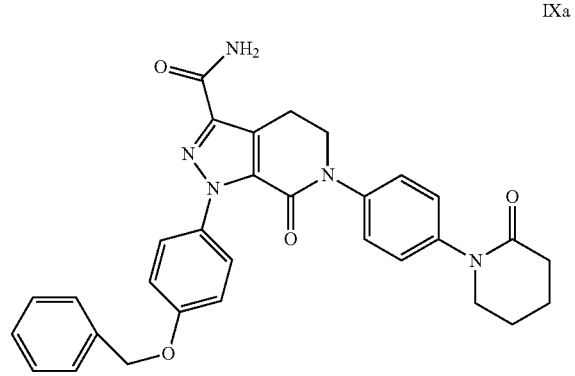

IXa

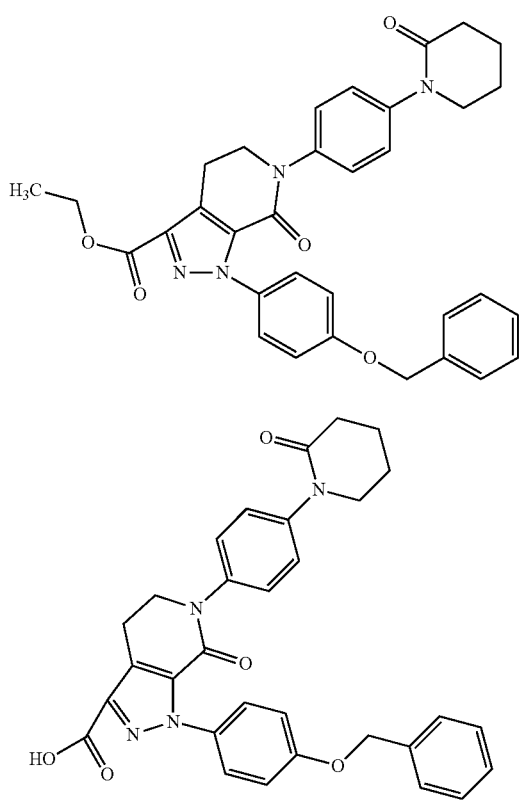

VII

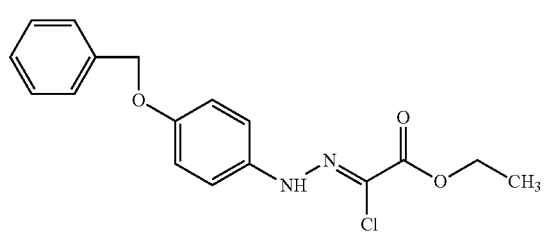

VI

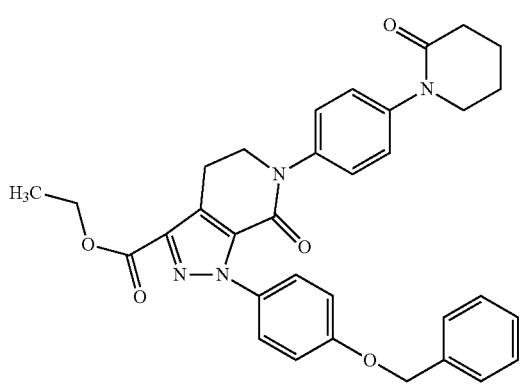

VII in the preparation of apixaban.

In one embodiment, the present invention provides a compound selected from the following:

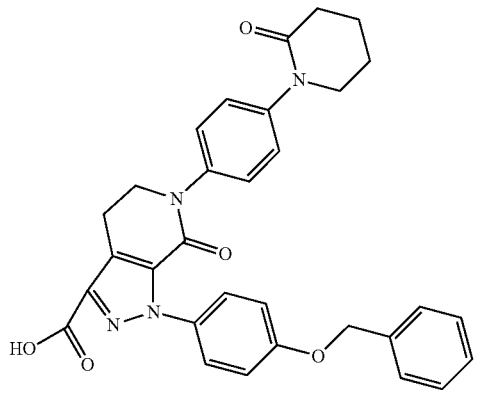

VIII

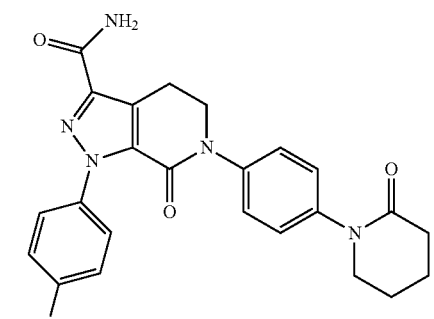

IXa

In one embodiment, the present invention provides a 1-(4-benzyloxy-phenyl)-7-oxo-6-[4-(2-oxo-piperidin-1-yl)-phenyl]-4;5,6,7-tetrahydro-1H-pyrazolo [3,4-c]pyridine-3-carboxylic acid, a compound of formula VII characterized by 1H NMR (300Mhz,CDCl$_3$) having peaks at 1.93 (4H, m, N—CH$_2$CH$_2$CH$_2$CH$_2$CO), 2.55(2H,m, N—CH$_2$CH$_2$CH$_2$CH$_2$CO), 3.35-3.39 (2H, t, CH$_2$CH$_2$N), 3.59 (2H, m, N—CH$_2$CH$_2$CH$_2$CH$_2$CO), 3.82 (3H,s,Ar—OCH$_3$), 4.11 (2H, t, CH$_2$CH$_2$N), 5.59 (1H, s, N—H), 6.87 (1H, s, N—H), 6.92-6.95(2H, dd, Ar—H), 7.23 (2H, dd, Ar—H), 7.32-7.35 (2H, dd, Ar—H), 7.45-7.48 (2H, dd, Ar—H).

In one embodiment, the present invention provides Preparation of 1-(4-Benzyloxy-phenyl)-7-oxo-6-[4-(2-oxo-piperidin-1-yl)-phenyl]-4,5,6,7-tetrahydro-1H-pyrazolo [3,4-c] pyridine-3-carboxylic acid amide, a compound of formula VIII characterized by 1H NMR (300 Mhz,CDCl$_3$) having peaks at 1.92 (4H, m, N—CH$_2$CH$_2$CH$_2$CH$_2$CO), 2.5-2.6 (2H,m, N—CH$_2$CH$_2$CH$_2$CH$_2$CO, merged with solvent peaks), 3.32-3.36 (2H, t, CH$_2$CH$_2$N), 3.59 (2H, m, N—CH$_2$CH$_2$CH$_2$CH$_2$CO), 4.0-4.08 (2H, t; CH$_2$CH$_2$N), 5.57 (1H, s, N—H), 6.70-6.73(2H, dd, Ar—H), 6.88 (1H, s, N—H), 7.23-7.38 (6H, m, Ar—H).

In one embodiment, the present invention provides 1-(4-hydroxy-phenyl)-7-oxo-6-[4-(2-oxo-piperidin-1-yl)-phenyl]-4,5,6,7-tetrahydro-1H-pyrazolo [3,4-c]pyridine-3-carboxylic acid amide, a compound of formula IXa characterized by 1H NMR (300 Mhz,DMSOd$_6$) having peaks at 1.84 (4H, m, N—CH$_2$CH$_2$CH$_2$CH$_2$CO), 2.38(2H, m, N—CH$_2$CH$_2$CH$_2$CH$_2$CO), 3.17-3.19 (2H, t, CH$_2$CH$_2$N), 3.58 (2H, m, N—CH$_2$CH$_2$CH$_2$CH$_2$CO), 4.0-4.06 (2H, t, CH$_2$CH$_2$N), 5.16 (2H, s, PhCH$_2$), 5.75 (2H, s, N—H), 7.05-7.08(2H, dd, Ar—H), 7.25-7.54 (10H, m, Ar—H), 7.73 (1H, br, Ar—H).

In one embodiment, the present invention provides a process for the preparation of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester, a compound of formula IV, comprising:

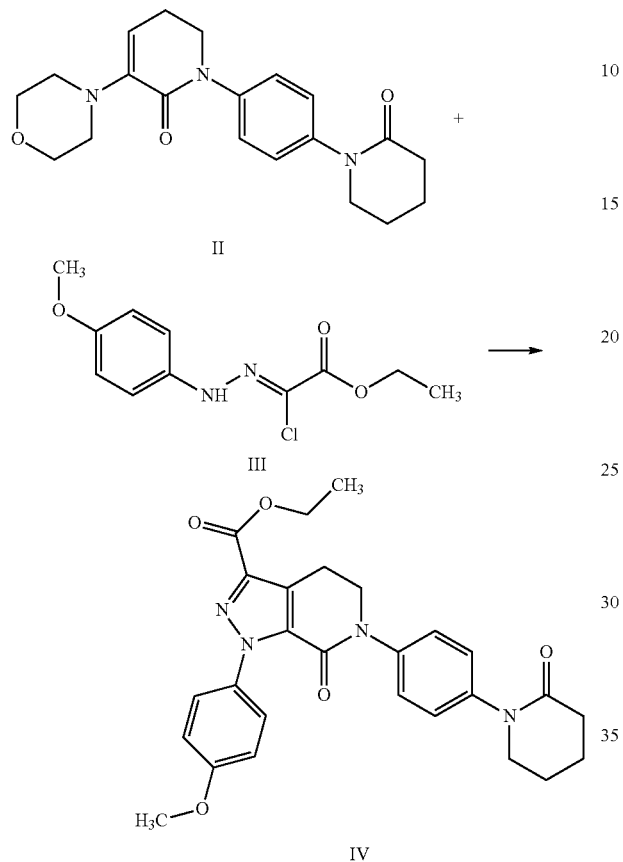

reacting a compound of formula II with a compound of formula III wherein the isolation process neither includes chromatographic separation nor chromatographic purification.

In one embodiment, the present invention provides a process for the preparation of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester, a compound of formula IV comprising reacting a compound of formula II with a compound of formula III in a suitable solvent.

A suitable solvent may be selected from, but is not limited to halogenated hydrocarbons such as methylene chloride, ethylene chloride, chloroform and carbon tetrachloride; alcohols such as methanol, ethanol, n-propyl alcohol, 2-propanol, tert-butanol; esters such as ethyl acetate, isopropyl acetate and butyl acetate; hydrocarbons such as benzene, toluene, cyclohexane and toluene; or mixtures thereof Preferably, the solvent is ethyl acetate.

The reaction may be carried out in the presence of a suitable organic or an inorganic base. The inorganic base, may be selected from but is not limited to hydroxides such as sodium hydroxide, potassium hydroxide; carbonates such as sodium carbonate, potassium carbonate; bicarbonates such as sodium bicarbonate, potassium bicarbonate, alkoxides such as sodium methoxide, potassium tertiary butoxide, hydrides such as sodium hydride. The organic base may be triethyl amine, trimethyl amine, pyridine, dimethyl amino pyridine. Preferably, the base is triethylamine.

In one embodiment, the reaction may be optionally carried out in the presence of a catalyst. A suitable catalyst may be selected from tetrabutyl ammonium bromide, tetrabutyl ammonium chloride, potassium iodide, sodium iodide, lithium iodide, sodium bromide and potassium bromide. Preferably, the catalyst is potassium iodide.

The reaction transpires at a temperature of about 0° C. to about reflux temperature of the solvent. Preferably the reaction transpires at about reflux temperature of the solvent.

In one embodiment, the present invention provides a process for the preparation of a compound of formula IV, comprising reacting a compound of formula II with a compound of formula III in the presence of triethylamine in ethyl acetate. The reaction mixture is heated to reflux temperature for a period of about 10 to 30 hours. Preferably, the reaction transpires over a period of about 24 hours. Then the compound of formula IV is isolated by aqueous extraction using sodium carbonate, dilute hydrochloric acid and isopropyl ether. The distillation of the resulting isopropyl ether solution results to a compound of formula IV with more than 99% purity.

In one embodiment, the present invention provides a process for the preparation of apixaban, compound of formula I, comprising amidating compound of formula IV to a compound of formula I in the presence of a suitable solvent/s.

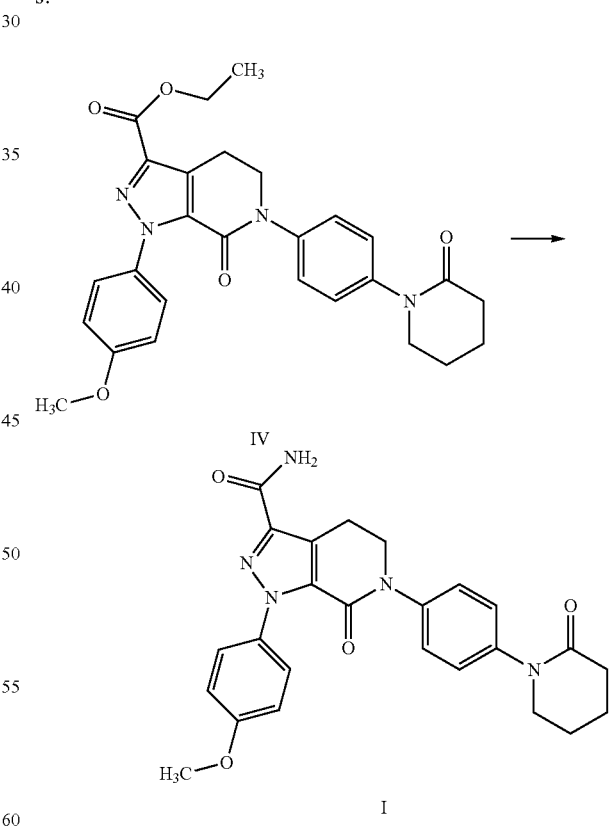

A suitable solvent may be selected from, but are not limited to nitriles such as acetonitrile, propionitrile and the like; aprotic solvents such as dimethyl sulfoxide, formamide, dimethyl formamide, dimethylacetamide and the like; hydrocarbons such as toluene, xylene, cyyclohexane; alcohols such as methanol, ethanol, isopropanol, butanol and the like; Esters such as ethylacetate, butylacetate, isopropylacetate and the like and mixtures thereof The reaction may be carried out in the presence of a suitable organic or an inorganic base. The inorganic base may be selected from but is not limited to hydroxides such as sodium hydroxide, potassium hydroxide; carbonates such as sodium carbonate, potassium carbonate; bicarbonates such as sodium bicarbonate, potassium bicarbonate, alkoxides such as sodium methoxide, potassium tertiary butoxide, hydrides such as sodium hydride; organic base such as triethyl amine, trimethyl amine, pyridine, dimethyl amino pyridine. Preferably, the base is sodium methoxide.

In one embodiment, the present invention provides a process for the preparation of compound of formula I, comprising dissolving compound of formula IV in dimethylsulfoxide and formamide. The reaction mixture is cooled to a temperature of about −5 to about 20° C.

Preferably the reaction mixture is cooled to a temperature of about 0-5° C. Sodium methoxide was added to the reaction mixture.

Apixaban, compound of formula I was isolated by methods known the art such as filtration and centrifugation.

In one embodiment, the present invention provides apixaban wherein apixaban obtained from the above process contains less than 0.1% of any of the impurity at relative retention time (RRT) 1.19, 1.46 and of a compound of formula V, as measured by high performance liquid chromatography(HPLC),

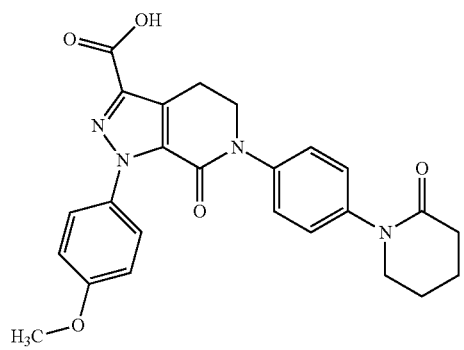

V

In one embodiment, the present invention provides apixaban wherein apixaban obtained in the process described above contains less than 0.1% of the impurity at RRT 1.19, 1.46 and of a compound of formula V, as measured by HPLC,

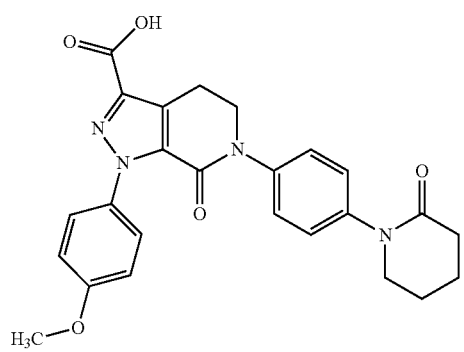

V

In one embodiment, the present invention provides apixaban having less than 0.1% of compound of formula V, as measured HPLC,

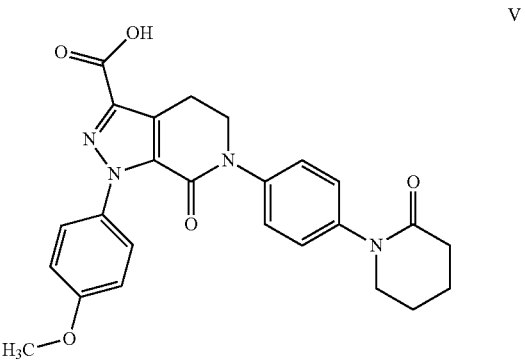 [SMILES: COc1ccc(-n2nc(C(=O)O)c3c2C(=O)N(c2ccc(N4CCCCC4=O)cc2)CC3)cc1]

V

In one embodiment, the present invention provides apixaban having no detectable impurity at RRT 1.19 and 1.46, as measured by HPLC.

Particle size plays an important role in the solubility properties of an active pharmaceutical ingredient (API). It is recognized that there is an inverse relationship between surface area and particle size; where the smaller the particle size, the higher the surface area. Whereupon, the available surface area for drug dissolution correlates to the rate of dissolution and solubility. A greater surface area enhances both the solubility and the rate of dissolution of a drug, which in turn, may improve its bioavailability and potentially its toxicity profiles.

In one embodiment of the present invention provides a process for preparing apixaban having $D_{90}$ of about 150μ. Preferably, having $D_{90}$ of about 100μ.

Particle size of apixaban may be further adjusted by employing known methods of particle size reduction like compaction, milling or micronizing and sorting the milled product according to particle size.

The particle size distribution of apixaban was determined by laser diffraction on Malvern Mastersizer 2000.

In one embodiment, the present invention provides apixaban having a purity of about 99.9% as measured by HPLC.

Apixaban can be prepared from compound of formula IV, by any method known in the art. Illustratively, it is described in U.S. Pat. No. 6,919,451, which is included by reference herein, in its entirety.

Instrumental Settings for XRPD:

The measurements were performed on Philips X-Ray Diffractometer model XPERT-PRO (PANalytical) Detector: X'celerator [1] using Cu lamp with type and wavelength of the X-ray radiation: K-Alpha1 [A] and 1.54060 under the following conditions: Generator settings: 40 mA/45 kV, Time per step: 50, Step size: 0.0170, Peak width 2.00 and start angle (°) 2.0 and End angle: 50.0, Scan type: continuous; measurement performed at 25° C. The XRPD instrument is calibrated using NIST SRM 6-40C silicon standard and NIST SRM 1976 Alumina.

Sample preparation: About 20mg of sample was taken and used to fill the groove onto silicon zero background holder using Top-loading technique. The sample holder was then loaded between the X-ray optics-path and scanned using the below described parameters. The obtained powder X-ray diffraction profiles were integrated using High Score Plus Software.

Instrumental Settings for HPLC:
Related substances by HPLC: High performance liquid chromatography (HPLC) was performed with the conditions described below for detecting chemical purity:
Reagents, Solvents and Standards: Water (Milli Q or equivalent), Ammonium acetate (Chromatographic Conditions, (HPLC Grade), Acetonitrile (HPLC Grade), Acetic acid (HPLC Grade).
Chromatographic Conditions
Apparatus: A High Performance Liquid Chromatograph equipped with quaternary gradient pumps, variable wavelength UV detector attached with data recorder and integrator software.
Column: Inertsil ODS 3V, 250×4.6mm, 5μ
Column temperature: 30° C.
Mobile Phase: Mobile phase A=Buffer: Acetonitrile (90:10, v/v)
Buffer: 0.01M Ammonium acetatein water. Adjust pH to 6.5 with diluted Glacial acetic acid. Mobile phase B=Acetonitrile

| Time (min.) | % Mobile Phase A | % Mobile Phase B |
|---|---|---|
| 0.01 | 85 | 15 |
| 40 | 30 | 70 |
| 45 | 30 | 70 |
| 47 | 85 | 15 |
| 55 | 85 | 15 |

Diluent: Water: Acetonitrile (50: 50, v/v)
Flow Rate: 1.0 mL/minute
Detection: UV 230 nm
Injection Volume: 10 μL
The retention time of apixaban is about 17.7 minutes under these conditions
Instrumental Settings for DSC: The DSC thermogram was measured by a Differential Scanning calorimeter (DSC 822, Mettler Toledo) at a scan rate of 10° C. per minute in the temperature range of range is "30° C. to 300° C". The DSC module was calibrated with Indium and zinc standard.
Method: An empty aluminum standard 40 μl pan was taken and put on the microbalance. Tared and weighed approximately about 2.0-3.0 mg of sample. The cover or lid of the pan was slightly pierced and sealed. The sample pan was placed in the left position of mark 'S' and empty pan was placed in the right position on mark 'R' of the DSC sensor. The furnace lid was placed. The method was selected.
Instrumental settings for TGA: Instrument Name: TGA Q 500; Method: 5-8 mg of sample was taken in platinum pan and heated at 10° C/minute from room temperature to 250° C.
The following examples are provided to enable one skilled in the art to practice the invention and are merely illustrative of the invention. The examples should not be read as limiting the scope of the invention.

EXAMPLES

Example I

Preparation of 1-(4-methoxy-phenyl)-7-oxo-6-[4-(2-oxo-piperidin-1-yl)-phenyl]-4,5,6,7-tetrahydro-1H-pyrazolo [3,4-c]pyridine-3-carboxylic acid ethyl ester In 3 lit four neck equipped round bottomed flask (RBF) equipped, ethyl acetate (2.5L), 3-morpholino-1-[4-(2-oxopiperidin-1-yl)phenyl] -5,6-dihydropyridin-2(1H)-one (50gm,), acetic acid, 2-chloro-2-[-(4-methoxyphenyl)hydrazinylidene],ethyl ester (36.1 gm) triethyl amine (57 gm) and potassium iodide (2.4 gm) were added sequentially at about 25-30° C. The reaction mass was heated to about 75-80° C. for about 24 hrs. After completion, the reaction mass was cooled to about 0-5° C. and dilute hydrochloric acid was added slowly to the reaction mass at about 0-5° C. The temperature of the reaction mass was raised to about 25-30° C. and stirred for 2 hrs. Water was added to the reaction mass and stirred for 15 min. The layers were separated and the organic layer was washed with aq. sodium carbonate solution followed by water. The organic layer was partially concentrated under vacuum and cooled to about 25-30° C. Isopropyl ether was added to the reaction mass and stirred for 1 hr. The precipitated solid was filtered and washed with isopropyl ether. The solid was dried under vacuum at 45-50° C. for 12 hrs to afford 54 gm of 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (HPLC purity>99%)

Example II

Preparation of 1-(4-methoxy-phenyl)-7-oxo-6-[4-(2-oxo-piperidin-1-yl)-phenyl]-4,5,6,7-tetrahydro-1H-pyrazolo [3,4-c]pyridine-3 -carboxylic acid amide (Apixaban)

A solution of 1-(4-methoxy-phenyl)-7-oxo-6-[4-(2-oxo-piperidin-1-yl)-phenyl]-4,5,6,7-tetrahydro-1H-pyrazolo[3, 4-c]pyridine-3-carboxylic acid ethyl ester (35 gm, 0.072 mmol) in dimethyl sulphoxide (175 ml) and formamide (32.26 gm, 0.72 mmol) was cooled to 0-5° C. and sodium methoxide solution (31 gm) was added drop wise at 0-5° C. and stirred for 30 min. The temperature of the reaction mass was raised to 25-30° C. and stirred for 2hrs. After completion of reaction, water was added to the reaction mass and stirred for 1 hr. The precipitated solid was filtered and washed with water and methyl tert-butyl ether. The wet cake was dissolved in a mixture of methylene dichloride and methanol (7:3) (900 ml) and washed with 5% aq. NaOH solution. The organic layer was washed with water and concentrated under vacuum. The obtained solid was taken in acetone and stirred for 1 hr. The solids were filtered and washed with acetone. The solid material was dried under vacuum at about 45-50° C. for 12hrs to afford 28$_g$m of apixaban (HPLC purity>99%)

Example III

Crystallization of Apixaban

In 2.0L 4-neck flask a suspension of apixaban (30 gm) in a mixture of acetone and demineralised water (8:2, 900 ml) was heated to 55-60° C. to get a clear solution. Norit charcoal (1.5 gm) was added to the clear solution and stirred for 1 hr. The reaction mass was filtered through hyflo at 50-60° C. The filtrate was gradually cooled to 10-15° C. and maintained for 1 hr. The precipitated solids were filtered and washed with acetone. The solids were dried under vacuum at 45-50° C. for 12 hrs to afford 23 gm apixaban. (HPLC>99.9%.) PSD: d(10):4.27 μm,d(50):26.56 μm,d(90): 75.32 μm Example IV Crystallization of Apixaban Apixaban (lgm) was dissolved in isopropyl alcohol (170 ml) at about reflux temp. After cooling the reaction mass, the crystallized product was collected by filtration and dried.
PSD: d (10):13 μm,d(50):34 μm,d(90):62 μm.

Example V

Apixaban (1 gm) was dissolved in methanol (40 ml) at about reflux temp. After cooling the reaction mass, the crystallized product was collected by filtration and dried under vacuum below 50° C.

Example VI

Apixaban (1 gm) was dissolved in a mixture of methanol and water [(8:2),30 ml] at about reflux temp. After cooling the reaction mass, the crystallized product was collected by filtration and dried

Example VII

Apixaban (1 gm) was dissolved in a mixture of THF and water [(8:2),30 ml] at about 60-65° C.After cooling the reaction mass the product crystallized was collected by filtration and dried.

Example VIII

Apixaban (1 gm) was dissolved in a mixture of DMF and water [(8:2),10 ml] at about 60-65° C.After cooling the reaction mass the product crystallized was collected by filtration and dried.

Example IX

Apixaban (1 gm) was dissolved in DMSO (10 ml) at a temperature of about 60-65° C. To this water (20 ml) was added as anti-solvent. After cooling the reaction mass the product crystallized was collected by filtration and dried under vacuum.PSD: d(10):7.03 μm,d(50):20.07 μm,d(90): 53.32 μm

Example X

Apixaban (1 gm) was dissolved in ethylene glycol (10 ml) at 75-80° C. After cooling the reaction mass, the product crystallized was collected by filtration and dried under vacuum.

Example XI

Apixaban (1 gm) was dissolved in a mixture of ethanol and water [(8:2),20 ml] at reflux. After cooling the reaction mass the product crystallized was collected by filtration and dried under vacuum.

Example XII

Apixaban (1 gm) was dissolved in a mixture of ethanol and isopropyl alcohol [(6:4),150 ml] at 78-80° C.After cooling the reaction mass the product crystallized was collected by filtration and dried under vacuum

Example XIII

Apixaban (01 gm) was dissolved in a mixture of tetrahydrofuran and methanol [(8:2),90 ml] at 60° C.After cooling the reaction mass the product crystallized was collected by filtration and dried under vacuum

Example XIV

Apixaban (1 gm) was dissolved in a mixture of isopropyl alcohol and methanol [(8:2),170 ml] at 60° C.After cooling the reaction mass the product crystallized was collected by filtration and dried under vacuum

Example XV (Form IV)

Apixaban (1 gm) was dissolved in acetic acid (10 ml) at 25-30° C. and water (12 ml) was added as anti-solvent. The precipitated product was collected by filtration and dried under vacuum.
PXRD 2θ values: 5.9, 7.4, 9.0, 11.7, 13.5, 13.9, 15.8, 16.1, 16.7, 17.5, 17.9, 18.7, 19.6, 20.0, 21.7, 22.2, 23.6, 24.6, 25.1, 25.8, 26.6, 27.4, 27.7, 28.5, 29.2 and 30.1 ±0.2 degrees 2Θ.

Example XV (Form IV)

Apixaban (1 gm) was dissolved in dimethylformamide (10 ml) at 40-45° C. and water (20 ml) was added as anti-solvent. The precipitated product was collected by filtration and dried under vacuum.

Example XVI (Form IV)

Apixaban (01 gm) was dissolved in a mixture of IPA: water [(8:2), 20 ml] at 80° C.The reaction mass was cooled to 25-30° C. The precipitated product was collected by filtration and dried under vacuum.

Example XVII

Preparation of 1-(benzyloxy)-4-nitrobenzene

In a clean round bottomed flask, acetone (1.0 L), 4-nitrophenol (100 g), potassium carbonate (70 g) benzyl bromide (127.8 g) were added sequentially at about 25-30° C. The reaction mass was heated to about 50-60° C. for about 8-12 hrs. After completion, the reaction mass was cooled to about 25-30° C. and water was added slowly to the reaction mass. The temperature of the reaction mass was maintained at about 25-30° C. and stirred for 2 hrs. The precipitated product was filtered and washed with water. The titled compound was dried under vacuum at 40-50° C. for 15-20 hrs to afford 155 gms of 1-(benzyloxy)-4-nitrobenzene.

Example XVIII

Preparation 4-(benzyloxy)aniline

In a clean round bottomed flask, ethanol (1.0 L), 1-(benzyloxy)-4-nitrobenzene, sodium sulfide (183 g) were added sequentially at about 25-30° C. The reaction mass was heated to about 70-80° C. for about 8-12 hrs. After completion, the reaction mass was cooled to about 25 -30° C. and water was added to the reaction mass. Reaction mass was extracted with ethyl acetate and organic phase was washed with brine solution. Ethyl acetate was distilled under vacuum. Hexane was charged to residue obtained and stirred for 1 hr. The solid was filtered and washed with hexane. The titled compound was dried under vacuum at 35-40° C. for 10-12 hrs to obtain 70 gm of 4-(benzyloxy) aniline.

Example XIX

Preparation ethyl (2Z)-{[4-(benzyloxy) phenyl] hydrazono}(chloro)acetate

In a clean round bottomed flask, ethanol (175 ml) and con hydrochloric acid (175 ml) were charged and stirred for 5-10 min. 4-(benzyloxy) aniline was added and reaction mass was chilled to −5° C. Sodium nitride solution was added slowly (26.6 g in 210 ml water) and temp was maintained about 1 hr. Ethyl chloroacetoacetate and sodium acetate were charged and reaction mass was stirred at 0-5 ° C. for 1 hr. A mixture of water and ethanol was added to the reaction mass and the temperature of reaction was raised to about 25-30° C. and stirred for 2 hrs. The precipitated solid was filtered and washed with ethanolic water. The solid was dried under vacuum at. 40-45° C. for 12-16 hrs to obtain 36 g of ethyl (2Z)-{[4-(benzyloxy) phenyl] hydrazono} (chloro)acetate.

Example XX

Preparation of 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester In a clean round bottomed flask ethyl acetate (525 ml), ethyl (2Z)-{[4-(benzyloxy) phenyl] hydrazono}(chloro)ac-etat (35 gm), potassium iodide (1.73 g), 3-morpholino-1-[4-(2-oxopiperidin-1-yl)phenyl]-5,6-dihydropyridin-2(1H)-one (31.82 g) and triethylamine (42.63 g) were added at about 25-30° C. The reaction mass was heated to about 75-80° C. for about 10-15 hrs. After completion, the reaction, mass was cooled to about 0-5° C. and dilute hydrochloric acid was added slowly to the reaction mass. The temperature of the reaction mass was raised to about 25-30° C. and stirred for 5-7 hrs. Ethyl acetate and water were added to the reaction mass and stirred for 15 min. The layers were separated and the organic layer was washed with aq. sodium carbonate solution followed by water and brine solution. The organic layer was concentrated under vacuum and cooled to about 25-30° C. Di isopropyl ether was added to the reaction mass and stirred for 1 hr. The precipitated solid was filtered and washed with di isopropyl ether. The solid was dried under vacuum at 45-50° C. for 12 hrs to obtain 54 gm of 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester.

Example XXI

Preparation of 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid In a clean round bottomed flask, methanol (100 ml), 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-carboxyli c acid ethyl ester (log) and aq. Sodium hydroxide solution (2.83 g NaOH in 6 ml water) were added at about 25-30° C. The reaction mass was stirred to about 25-30° C. for about 2-4 hrs. After completion, methanol was distilled out from reaction mass and water was charged to the residue and pH of mass was adjusted to 2-3 with dilute hydrochloric acid. MDC (methylene dichloride) and water were added to the reaction mass and stirred for 15 min. The layers were separated and the aqueous layer extracted with MDC. Organic layer was washed with by water and brine solution. The organic layer was concentrated under vacuum and cooled to about 25-30° C. MTBE (methyl tert butyl ether) was added to the reaction mass and stirred for 1 hr. The precipitated solid was filtered and washed with MTBE. The solid was dried under vacuum at 40-45° C. for 10-12hrs to obtain 8.4 gm of 1-(4-benzyloxy-phenyl)-7-oxo-6-[4-(2-oxo-piperidin-1-yl)-phenyl]-4,5,6,7-tetrahydro-1H-pyrazolo [3,4-c]pyridine-3-carboxylic acid.

Example XXII

Preparation of 1-(4-Benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide In a clean round bottomed flask, ethyl Acetate (150 ml), 1-(4-benzyloxy-phenyl)-7-oxo-6-[4-(2-oxo-piperidin-1-yl)-phenyl]-4,5,6,7-tetrahydro-1H-pyrazolo [3,4-c]pyridine-3-carboxylic acid (10 g), triethylamine (3.77 g) were added sequentially at about 25-30° C. The reaction mass was chilled to about 0-5° C. and isobutyl chloroformate (4.34 g) was added slowly. The temperature of reaction mass was increased to 20-25° C. and reaction mass was stirred for about 2-4 hrs. Aqueous ammonia solution (150 ml) was charged and the precipitated solid was filtered and washed with mixture of methanol and water. The solid was dried under vacuum at 40-45° C. for 10-12hrs to obtain 5.5 gm of 1-(4-benzyloxy-phenyl)-7-oxo-6-[4-(2-oxo-piperidin-1-yl)-phenyl]-4,5,6,7-tetrahydro-1H-pyrazolo [3,4-c]pyridine-3 -carboxylic acid amide.

Example XXIII

Preparation of 1-(4-Benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide In 500 ml four neck equipped round bottomed flask (RBF), DMF (dimethyl formamide, 60 ml), 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (10 g), formamide (7.97 g) were added sequentially at about 25-30° C. The reaction mass was cooled to about 0-5° C. 25% sodium methoxide solution (50 ml) was added slowly. The reaction mass was stirred for 1-3 hr. After completion of reaction, water was added slowly to the reaction mass at about 15-30° C. and stirred for 1 hr. The precipitated solid was filtered and washed with water. The solid was dried under vacuum at 40-45° C. to obtain 5.3 gm of 1-(4-benzyloxy-phenyl)-7-oxo-6-[4-(2-oxo-piperidin-1-yl)-phenyl]-4,5,6,7-tetrahydro-1H-pyrazolo[3,4-c]pyridine-3-amide.

Example XXIV

Preparation of 1-(4-Benzyloxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide In a clean round bottomed flask, DMSO (dimethyl sulphoxide, 60 ml), 1-(4-benzyloxy-phenyl)-7-oxo-6-[4-(2-oxo-piperidin-1-yl)-phenyl] -4,5,6,7-tetrahydro-1H-pyrazolo[3,4-c]pyridine-3-carboxylic acid ethyl ester (10 g), formamide (7.97 g) were added sequentially at about 25-30° C. The reaction mass was cooled to about 0-5° C. and 25% sodium methoxide solution (50 ml) was added slowly. The reaction mass was stirred for 1-3 hr. After completion of reaction, water was added slowly to the reaction mass at about 15-30° C. and pH was adjusted to 7-7.5 by dil. HCl. Product was extracted with methylene dichloride (MDC). MDC layer was washed with dil. NaOH solution followed by brine solution. MDC was distilled out under vacuum and diisopropyl ether (DIPE, 50 ml) was charged and mass was stirred for one hr. The precipitated solid was filtered and washed with DIPE. The solid was dried under vacuum at 40-45° C. to obtain 5.2 gm of 1-(4-benzyloxy-phenyl)-7-oxo-6-[4-(2-oxo-piperidin-1-yl)-phenyl]-4,5,6,7-tetrahydro-1H-pyrazolo [3,4-c]pyridine-3-amide.

Example XXV

Preparation of Compound-VI: 1-(4-hydroxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide In a clean autoclave, methanol (210 ml), 1-(4-benzyloxy-phenyl)-7-oxo-6-[4-(2-oxo-piperidin-1-y1)-phenyl]-4,5,6,7-tetrahydro-1H-pyrazolo[3,4-c]pyridine-3-carboxylic acid amide 7.0 g., 10% Pd/C 1.0 g, acetic acid 7.0 ml. were charged. 5-7 kg hydrogen pressure was applied for 18-22 hr at 45-50° C. After completion of reaction, reaction mass was cooled to RT and catalyst was filtered. Clear filtrate was distilled under vacuum at 45-50° C. and water and methylene dichloride (MDC) were charged to the obtained residue. The pH of reaction mass was adjusted 7-7.5 with triethylamine. The organic and aqueous layer were separated. Aqueous layer was extracted with MDC. Combined organic layer was washed with brine solution and concentrated under vacuum. MTBE (methyl tertiary buty ether) was charged to the residue and stirred for 1.0 hr at 25-30° C. The product was filtered and wet cake was washed with MTBE, product was dried at 40-45° C. to obtain 4.5 gm of 1-(4-hydroxy-phenyl)-7-oxo-6-[4-(2-oxo-piperidin-1-yl)-phenyl]-4,5,6,7-tetrahydro-1H-pyrazolo [3,4-c]pyridine-3-amide.

Example XXVI

Preparation of Apixaban

In 250 ml four neck equipped round bottomed flask (RBF), acetone (100 ml), 1-(4-hydroxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide (10 g), potassium carbonate (4.65 g), dimethyl sulphate (DMS) (4.25 g) were charged. Reaction mass was stirred for 3-5 hr at 25-30° C. and after completion of reaction, water was added slowly. Reaction mass was stirred 1-2 hrs at 25-30° C. Solid obtained was filtered and washed with water 20 ml. The product was dried at 40-45° C. to obtain 4.5 gm of apixaban. HPLC purity 98.2%.

Example XXVII

Purification of Apixaban

In 250 ml four neck equipped round bottomed flask (RBF), MDC (210 ml), methanol (90 ml) and crude apixaban (10 g) were charged, reaction mass was stirred at 25-30° C. temp to get clear solution. NaOH solution (50 ml, 5% aqueous) was added to the clear reaction mass and layers were separated. Organic layer was again washed with NaOH solution followed by water wash. Organic layer was distilled and degassed to dryness to afford 8.5 gm residue. Acetone (221 ml) and water (59.5 ml) were added to the residue and heated to reflux temp and subjected to charcoal treatment, reaction mass was filtered and cooled to 25-30° C. The reaction mass was further cooed to 10-15° C. and stirred for 1-2 hr. Apixaban was filtered and washed with acetone and dried at 40-45° C. to afford 7.0 g Apixaban.

Example XXVIII

In 250 ml four neck equipped round bottomed flask (RBF), DMSO (80 ml) and crude apixaban 10 gm were heated to 70-80° C. to get clear solution. Reaction mass was filtered, filtrate was heated to 75-80 ° C. and 180 ml water was added slowly. Reaction mass was cooled to 25-30° C. and stirred 1-2 hrs. Apixaban obtained was filtered and washed with water. The product was dried at 40-45° C. to obtain apixaban 8 gm; purity. Purity: 99.9%, single max impiruty:0.05%

The invention claimed is:

1. A process for the preparation of a compound of formula I,

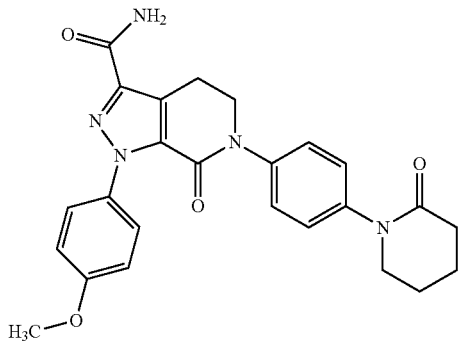

comprising:
a) deprotecting a compound of formula IX, Wherein R is selected from the group consisting of benzyl, optionally substituted benzyl, allyl, trityl, silyl and C(O)R1, wherein R1 is H, or lower alkyl to obtain a compound of formula X; and

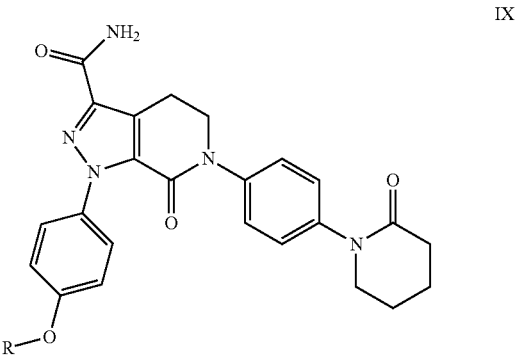

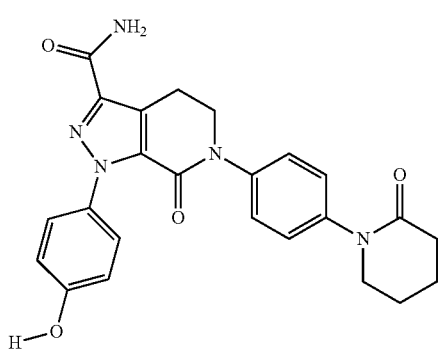

b) methylating the compound of formula X to obtain apixaban, a compound of formula I.

2. The process according to claim 1, wherein R is benzyl, and the compound of formula IX is of formula IXa

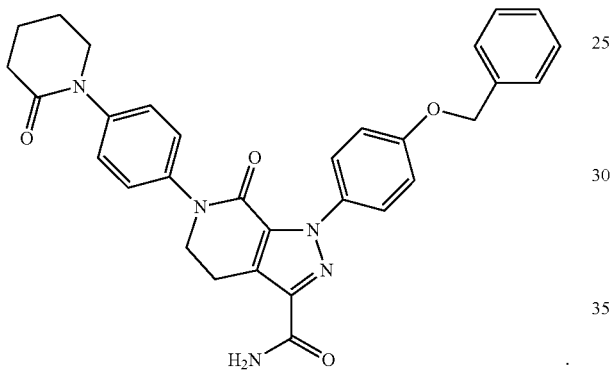

3. The process according to claim 2, Wherein in step a) R is benzyl, and the deprotection is carried out by hydrogenation.

4. The process according to claim 1, wherein in step b) the methylating agent is selected from the group consisting of methyl iodide, dimethyl sulphate, and dimethyl carbonate.

5. The process according to claim 2, wherein the compound of formula IXa is prepared by a process comprising;

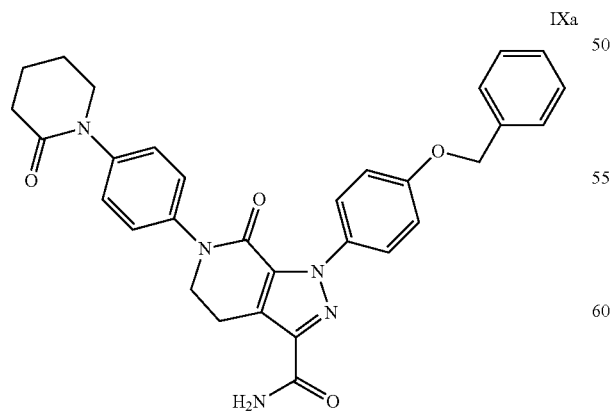

a) reacting a compound of formula II with a compound of formula VI to obtain a compound of formula VII; and

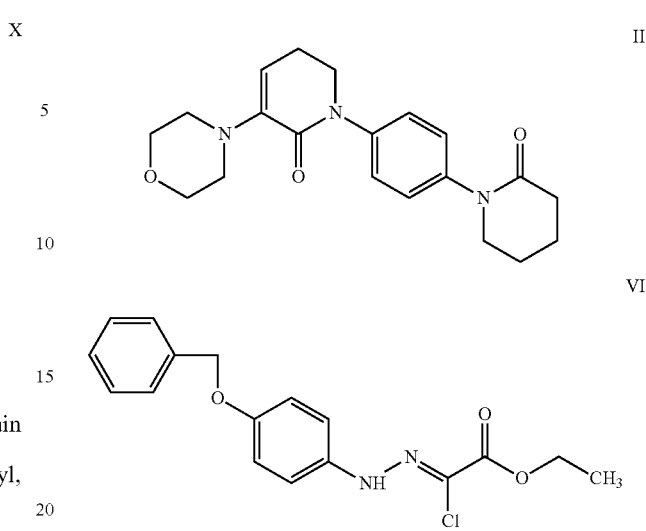

b) convening the compound of formula VII to a compound of formula IXa

6. The process according to claim 5, wherein in step b) the compound of formula VII is hydrolysed to obtain a compound of formula VIII

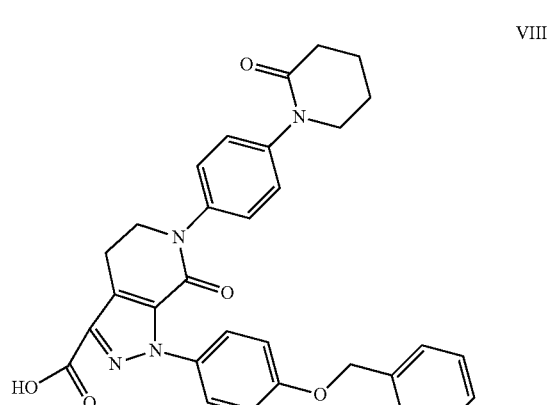

and then amidated to obtain a compound of formula IXa.

7. The process according to claim 1 further comprising purification of apixaban comprising treating crude apixaban with a base.

8. The process according to claim 7, further comprising:
isolating apixaban from a mixture of water and an organic solvent selected from the group consisting of alcohols, ethers, amides, esters, nitriles, sulfoxides, ketones, hydrocarbons, acetates and halogenated hydrocarbons.

9. The process according to claim 8, wherein the isolation comprises:
a) treating apixaban in a mixture of water and an organic solvent selected from the group consisting of alcohols, ethers, esters, amides, nitriles, sulfoxides, ketones, hydrocarbons, acetates and halogenated hydrocarbons to form a mixture;
b) optionally heating the mixture of step (a); and
c) crystallizing apixaban from the mixture.

10. The process according to claim 8, wherein the isolation comprises:
a) dissolving apixaban in a solvent selected from the group consisting of alcohols, ethers, esters, amides, nitriles, sulfoxides, ketones and hydrocarbons to form a solution;
b) adding water as an anti-solvent to the solution; and
c) crystallising apixaban from the above step (b).

11. The process according to claim 10, wherein apixaban is dissolved in DMSO and water is added as an anti-solvent.

12. The process according to claim 11, wherein the compound of formula VII or VIII is less than 0.1% w/w of apixaban, as measured by high performance liquid chromatography 13. A compound selected from the following

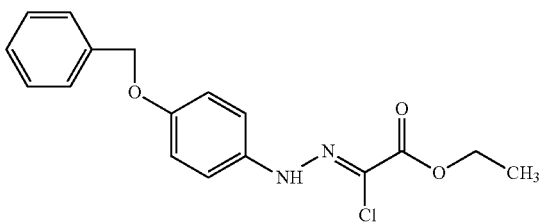

VI

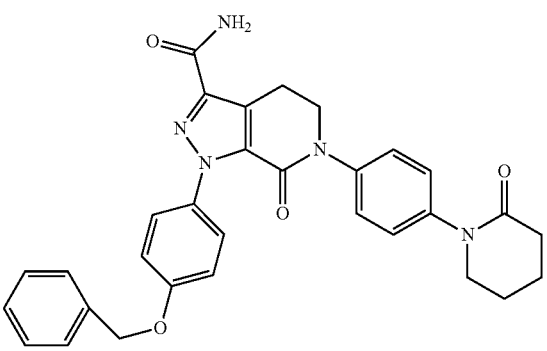

IXa

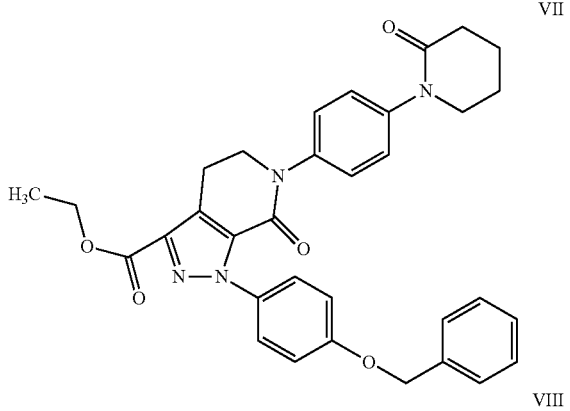

VII

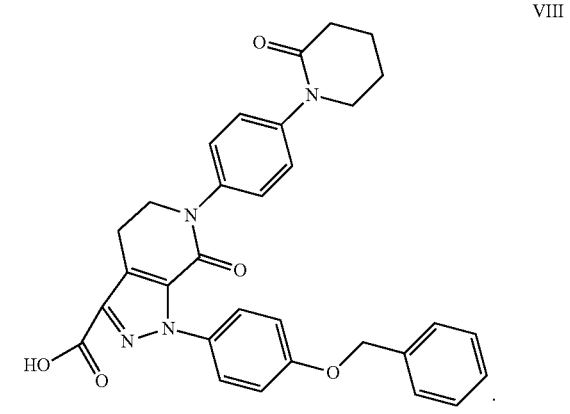 [SMILES: O=C(O)c1nn(-c2ccc(OCc3ccccc3)cc2)c2c1CCN(c1ccc(N3CCCCC3=O)cc1)C2=O]

VIII

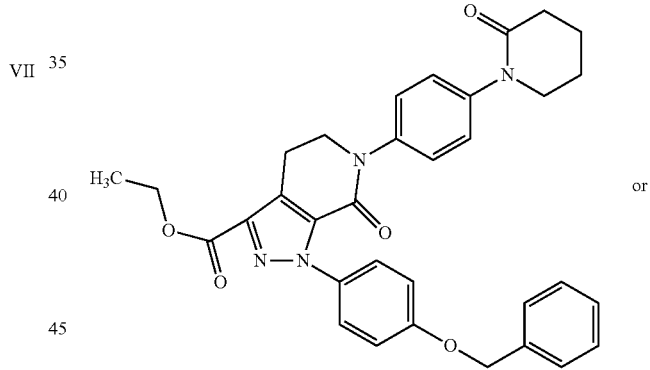

VII or VIII

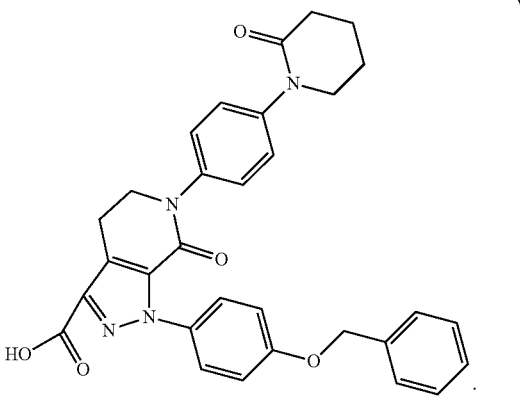

VIII

14. A process for the preparation of a compound of formula I,

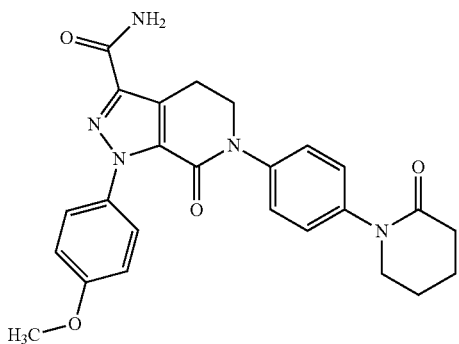

comprising the following steps:
(i) reacting a compound of formula II with a compound of formula VI to obtain a compound of formula VII,

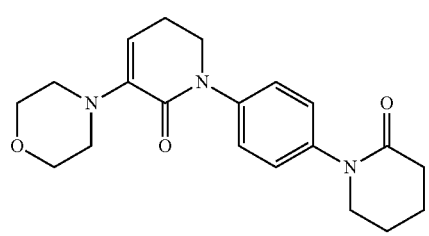

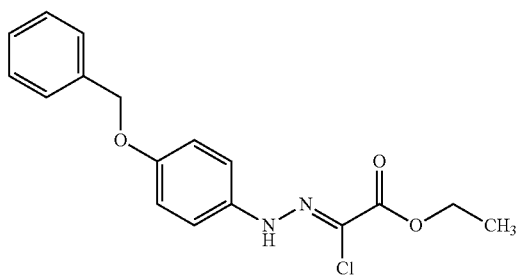

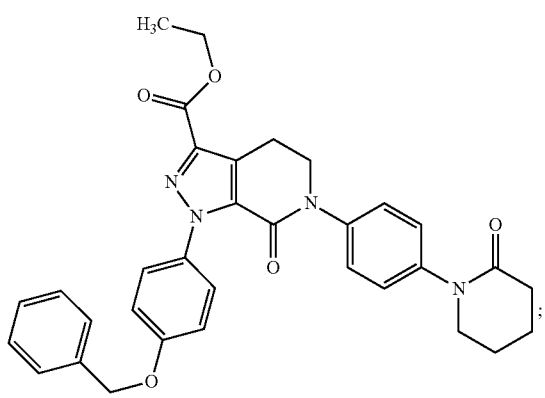

and
(ii) hydrolysing a compound of formula VII to the compound of formula VIII,

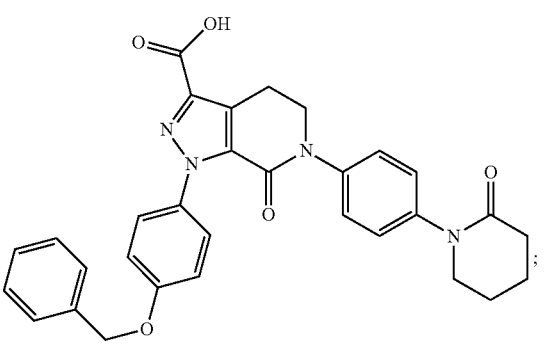

and
(iii) amidating a compound of formula VIII to obtain a compound of formula IXa,

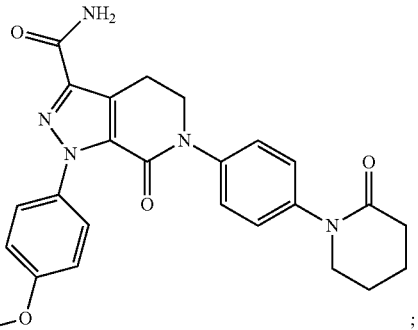

and, lastly
(iv) converting a compound of formula IXa to the compound of formula I.

* * * * *